United States Patent
Conrad

(10) Patent No.: US 8,404,439 B2
(45) Date of Patent: Mar. 26, 2013

(54) METHODS AND COMPOSITIONS FOR ISOLATING SMALL RNA MOLECULES

(75) Inventor: Richard C. Conrad, Austin, TX (US)

(73) Assignee: Applied Biosystems, LLC, Carlsbad, CA (US)

( * ) Notice: Subject to any disclaimer, the term of this patent is extended or adjusted under 35 U.S.C. 154(b) by 566 days.

(21) Appl. No.: 12/610,807

(22) Filed: Nov. 2, 2009

(65) Prior Publication Data

US 2010/0222564 A1   Sep. 2, 2010

Related U.S. Application Data

(63) Continuation of application No. 10/667,126, filed on Sep. 19, 2003, now abandoned.

(60) Provisional application No. 60/490,325, filed on Jul. 25, 2003.

(51) Int. Cl.
*C12Q 1/68* (2006.01)
*C07H 21/00* (2006.01)

(52) U.S. Cl. .................. 435/6.1; 536/22.1; 536/25.4

(58) Field of Classification Search .............. 435/6.1; 536/22.1, 25.4
See application file for complete search history.

(56) References Cited

U.S. PATENT DOCUMENTS

| | | | |
|---|---|---|---|
| 5,128,247 A | 7/1992 | Koller | |
| 5,155,018 A | 10/1992 | Gillespie et al. | |
| 5,196,182 A | 3/1993 | Ryan | |
| 5,234,809 A | 8/1993 | Boom et al. | |
| 5,260,048 A | 11/1993 | Ryan | |
| 5,480,972 A | 1/1996 | Avjioglu et al. | |
| 5,658,548 A | 8/1997 | Padhye et al. | |
| 5,808,041 A | 9/1998 | Padhye et al. | |
| 5,990,302 A | 11/1999 | Kuroita et al. | |
| 6,043,354 A | 3/2000 | Hillebrand et al. | |
| 6,110,363 A | 8/2000 | Hillebrand et al. | |
| 6,111,096 A | 8/2000 | Laugharn, Jr. et al. | |
| 6,168,918 B1 | 1/2001 | Satishchandran et al. | |
| 6,180,778 B1 | 1/2001 | Bastian et al. | |
| 6,218,531 B1 | 4/2001 | Ekenberg | |
| 6,248,535 B1 | 6/2001 | Danenberg et al. | |
| 6,387,695 B1 | 5/2002 | Evans et al. | |
| 6,428,963 B2 | 8/2002 | Danenberg et al. | |
| 2002/0028459 A1* | 3/2002 | Weisburg et al. | 435/6 |
| 2002/0094539 A1 | 7/2002 | Hornby et al. | |
| 2002/0139751 A1* | 10/2002 | Zhang et al. | 210/656 |
| 2002/0197629 A1 | 12/2002 | Gjerde et al. | |
| 2003/0138828 A1 | 7/2003 | Bost et al. | |
| 2003/0143732 A1 | 7/2003 | Fosnaugh et al. | |
| 2004/0191872 A1 | 9/2004 | Cheong et al. | |
| 2005/0054847 A1 | 3/2005 | Madden et al. | |
| 2009/0197307 A1 | 8/2009 | Madden et al. | |
| 2010/0222564 A1* | 9/2010 | Conrad | 536/25.41 |

FOREIGN PATENT DOCUMENTS

| | | |
|---|---|---|
| EP | 0389063 | 3/1990 |
| WO | WO98/04745 | 2/1998 |
| WO | WO98/59076 | 12/1998 |
| WO | WO93/57910 | 7/2003 |
| WO | 2005/012487 | 2/2005 |
| WO | WO 2005/012523 | 2/2005 |
| WO | WO2005/054466 | 6/2005 |

OTHER PUBLICATIONS

Allerson, C. et al., "A high-capacity RNA affinity column for the purification of human IRP1 and IRP2 overexpressed in *Pichia pastoris*," RNA, vol. 9, No. 3, pp. 364-374 (2003).
Anderson, A. et al., "HPCL purification of RNA for crystallography and NMR," RNA, vol. 2, No. 2; pp. 110-117 (1996).
Dickman, M.J. et al., "RNA footprinting analysis using ion pair reverse phase liquid chromatography," RNA, vol. 8, No. 2, pp. 247-251 (2002).
Hannon, G. J. et al., "RNA Interference," Nature, vol. 418, pp. 244-251 (2002).
Johansen, L.K. et al., "Silencing on the Spot. Induction and Suppression of RNA Silencing in the *Agrobacterium*-Mediated Transient Expression System," Plant Physiology, vol. 126, pp. 930-938 (2001).
Oefner, P.J. et al., "High-Resolution Liquid Chromatography of Fluorescent Dye-Labeled Nucleic Acids," Analytical Biochemistry, vol. 223, No. 1, pp. 39-46 (1994).
Paddison, P. et al., "Short hairpin RNAs (shRNAs) induce sequence-specific silencing in mammalian cells," Genes & Development, vol. 16, pp. 948-958 (2002).
Qiagen, "RNA/DNA Handbook," Qiagen, Nov. 1998.
European Communication pursuant to Article 94(3) mailed Aug. 5, 2008 in European Application No. 04779463.1 filed Jul. 30, 2004 entitled "Compositions and Methods for Preparing Short RNA Molecules and Other Nucleic Acids;" Inventor: Madden, et al (IVGN 365 EP).
International Search Report and Written Opinion mailed May 25, 2007 in International Application No. PCT/US04/24415 entitled "Compositions and Methods for Preparing Short RNA Molecules and Other Nucleic Acids;" Inventor: Madden, et al (IVGN 365 PCT).
International Preliminary Report on Patentability mailed Jun. 19, 2007 in International Application No. PCT/US04/24415 entitled "Compositions and Methods for Preparing Short RNA Molecules and Other Nucleic Acids;" Inventor: Madden, et al (IVGN 365 PCT).
USPTO issued Office Action mailed Mar. 13, 2007 in U.S. Appl. No. 10/902,704, filed Jul. 30, 2004 entitled "Methods and Compositions for Preparing Short RNA Molecules and Other Nucleic Acids;" Inventor: Madden, et al; (IVGN 365).
USPTO issued Final Office Action mailed Mar. 10, 2008 in U.S. Appl. No. 10/902,704, filed Jul. 30, 2004 entitled "Methods and Compositions for Preparing Short RNA Molecules and Other Nucleic Acids;" Inventor: Madden, et al; (IVGN 365).

(Continued)

*Primary Examiner* — Ethan C Whisenant

(57) ABSTRACT

The present invention concerns the use of methods and compositions for the isolation of small RNA molecules (100 nucleotides or fewer), such as microRNA and siRNA molecules. Such molecules are routinely lost in commonly used isolation procedures and therefore the present invention allows for a much higher level of enrichment or isolation of these small RNA molecules.

5 Claims, 7 Drawing Sheets

OTHER PUBLICATIONS

Ambion, The Basic: RNA Isolation, www.ambion.com/techlib/basics.rnaisol/index.html, 2006.

Finke et al., "An Improved Strategy and a Useful Housekeeping Gene for RNA Analysis from Formalin-Fixed, Paraffin-Embedded Tissues by PCR", *BioTechnigues*, vol. 14, No. 3, Mar. 1993, 448-453.

Jones et al., "Transition metal salts as adjuncts to formalin for tissue fixation", *Laboratory Investigation*, vol. 44, 1981, 32A.

Krafft et al., "Optimization of the isolation and amplification of RNA from formalin-fixed, parafffin-embedded tissues: The Armed Forces Institute of Pathology Experience and Literature Review", *Molecular Diagnosis*, vol. 2, No. 3, Sep. 1997, 217-230.

Lehmann et al., "Real-Time peR Analysis of DNA and RNA Extracted From Formalin-Fixed and Paraffin-Embedded Biopsies", *Methods* (Orlando), 25, No. 1, Dec. 2001, 409-418.

Novagen, "Thrombin Kits (TB 188 Aug. 1998)", Novagen, Online! 1998, http://www.emdbiosciences.com/docs/docs/PROT/tb188.pdf.

Palmieri et al., "Detection of Occult Melanoma Cells in Paraffin-Embedded Histologically Negative Sentinel Lymph Nodes Using a Reverse Transcriptase Polymerase Chain Reaction AssayII", *Journal of Clinical Oncology*, vol. 19; No. 5, Mar. 2001, 1437-1443.

Roche Instruction Manual, High Pure RNA Parrafin Kit, 2001.

Tollet-Egnell et al., "Gene Expression Profile of the Aging Process in Rat Liver: Normalizing Effects of Growth Hormone Replacement", *Molecular Endocrinology*, vol. 15, No. 2, Feb. 1, 2001, 308-318.

Gribanov, et al., "A Simple Method for RNA Isolation and Purification", *Bioorganicheskaya Khimiya*, vol. 23, No. 9, Sep. 1997, 763-765, Absrtract Only.

Abrahamsen et al., "Towards Quantitative mRNA Analysis in Paraffin-Embedded Tissues Using Real-Time Reverse Transcriptase-Polymerase Chain Reaction," *J. Mol. Diagn.*, 5(1):34-41, 2003.

Ambion, Inc., "mirVana miRNA isolation kit: instruction manual," http://www.ambion.com/techlib/ prot/fm_1560.pdf, 2004.

Ambion, Inc., "RiboPure WBC: instruction manual," http://web.archive.org/web/20030417123134/www. ambion.com/techlib/prot/fm_1903.pdf, 2003.

Ambion, Inc., "Silencer siRNA Construction Kit: large scale synthesis and purification of siRNAs," www.ambion.com, p. 1-10, 2003.

Ambros, V., "microRNAs: Tiny Regulators with Great Potential," *Cell*, 107:823-826, 2001.

Bock et al., "One-Step Extraction of RNA from Archival Biopsies," *Anal Biochem.*, 295(1):116-117, 2001.

Boom et al., "Rapid and simple method for purification of nucleic acids," *J. Clin. Microbiol.*, 28(3):495-503, 1990.

Carrington et al., "Role of microRNAs in plant and animal development," *Science*, 301:336-338, 2003.

Chomczynski and Sacchi, "Single-step method of RNA isolation by acid guanidinium thiocyanate-phenol-chloroform extraction," *Anal. Biochem.*, 162(1):156-159, 1987.

Coombs et al., "Optimisation of DNA and RNA extraction from archival formalin-fixed tissue," *Nucleic Acids Research*, 27(16):E12, 1999.

Fang et al., "Formalin Removal from Archival Tissue by Critical Point Drying," *Biotechniques*, 33(3):604, 606, 608-610, 2002.

Fire et al., "Potent ans specific genetic interference by double-stranded RNA in *Caenorhabditis elegans*," *Nature*, 391(6669):806-811, 1998.

Godfrey et al., "Quantitative mRNA Expression Analysis from Formalin-Fixed, Paraffin-Embedded Tissues Using 5' Nuclease Quantitative Reverse Transcription-Polymerase Chain Reaction," *J. Mol. Diagn.*, 2(2):84-91, 2000.

Hamilton and Baulcombe, "A species of small antisense RNA in posttranscriptional gene silencing in plants," *Science*, 286(5441):950-952, 1999.

Karsten et al., "An evaluation of tyramide signal amplification and archived fixed and frozen tissue in microarray gene expression analysis," *Nucleic Acids Research*, 30(2):E4, 2002.

Koopmans et al., "Optimization of extraction and PCR amplification of RNA extracts from paraffin-embedded tissue in different fixatives," *J. Virol. Methods*, 43(2):189-204, 1993.

Lagos-Quintana et al., "Identification of novel genes coding for small expressed RNAs," *Science*, 294(5543):853-858, 2001.

Lau et al., "An abundant class of tiny RNAs with probable regulatory roles in *Caenorhabditis elegans*," *Science*, 294(5543):858-862, 2001.

Lee and Ambros, "An extensive class of small RNAs in *Caenorhabditis elegans*," *Science*, 294(5543)862-864, 2001.

Lee et al., "The *C. elegans* heterochronic gene lin-4 encodes small RNAs with antisense complementarity to lin-4," *Cell*, 75(5):843-854, 1993.

Liu et al., "Archival Fixed Histologic and Cytologic Specimens Including Stained and Unstained Materials are Amedable to RT-PCR," *Diagn. Mol Pathol.* 11(4):222-227, 2002.

Masuda et al., "Analysis of chemical modification of RNA from formalin-fixed samples and optimization of molecular biology applications for such samples," *Nucleic Acids Research*, 27(22):4436-4443, 1999.

Moss, E., "RNA interference: It's a small RNA world," *Current Biology*, 11(19):R772-R775, 2001.

Pasquinelli et al., "Conservation of the sequence and temporal expression of let-7 heterochronic regulatory RNA," *Nature*, 408(6808):86-89, 2000.

Patterson and Guthrie, "An essential yeast snRNA with a U5-like domain is required for splicing in vivo," *Cell*, 49(5):613-624, 1987.

Peacock and Dingman, "Resolution of multiple ribonucleic acid species by polyacrylamide gel electrophoresis" *Biochemistry*, 6(6):1818-1827, 1967.

RNA STAT-60 Reagent, p. 1-4 (http://www.isotexdiagnostics.com/rna_stat-60_reagent.html, (2007).

Specht et al., "Quantitative Gene Expression Analysis in Microdissected Archival Formalin-Fixed and Paraffin-Embedded Tumor Tissue," *Am. J. Pathol.*, 158(2):419-429, 2001.

Stellrecht and Gandhi, "Concurrent isolation of ribosoma., messenger, and low molecular weight RNA," *Biotechniques*, 33(5):1122-1124, 2002.

Stratagene manual, "Mirco RNA Isolation Kit" 2000.

Tang et al., "A biochemical framwork for RNA silencing in plants," *Genes Dev.*, 17(1):49-63, 2003.

Timmons, "The long and short of siRNAs," *Mol. Cell.*, 10(3):435-437, 2002.

Van Deerlin et al., "Optimizing Gene Expression Analysis in Archival Brain Tissue," *Neurochem. Res.*, 27(10):993-1003, 2002.

Zamore et al., "RNAi: double-stranded RNA directs the ATP-dependent cleavage of mRNA at 21 to 23 nucleotide intervals," *Cell*, 101(1):25-33, 2000.

People's Republic of China First Office Action mailed Jun. 13, 2008 for Application No. 200480025190.7 entitled "Methods and Compositions for Isolating Small RNA Molecules;" Inventor: Richard C. Conrad; Applicant: Ambion Inc.

EPO Communication pursuant to Article 96(2) EPC mailed Jun. 2, 2006 for App No. 04779084.5-2403 entered into EP phase from PCT/US04/23850 entitled "Methods and Compositions for Isolating Small RNA Molecules;" Inventor: Richard C. Conrad; Applicant: Ambion Inc.

EPO Communication pursuant to Article 94(3) EPC mailed Jun. 12, 2008 for App No. 04779084.5-2403 entered into EP phase from PCT/US04/23850 entitled "Methods and Compositions for Isolating Small RNA Molecules;" Inventor: Richard C. Conrad; Applicant: Ambion Inc.

EPO Communication pursuant to Article 94(3) EPC mailed Apr. 14, 2010 for App No. 04779084.5-2403 entered into EP phase from PCT/US04/23850 entitled "Methods and Compositions for Isolating Small RNA Molecules;" Inventor: Richard C. Conrad; Applicant: Ambion Inc.

USPTO issued Office Action mailed Jan. 5, 2007 in U.S. Appl. No. 10/667,126, filed Sep. 19, 2003 entitled Methods and Compositions for Isolating Small RNA Molecules; Inventor: Richard C. Conrad.

USPTO issued Office Action mailed Aug. 23, 2007 in U.S. Appl. No. 10/667,126, filed Sep. 19, 2003 entitled Methods and Compositions for Isolating Small RNA Molecules; Inventor: Richard C. Conrad.

USPTO issued Final Office Action mailed Mar. 10, 2008 in U.S. Appl. No. 10/667,126, filed Sep. 19, 2003 entitled "Methods and Compositions for Isolating Small RNA Molecules;" Inventor: Richard C. Conrad.

USPTO issued Office Action mailed Oct. 28, 2008 in U.S. Appl. No. 10/667,126, filed Sep. 19, 2003 entitled "Methods and Compositions for Isolating Small RNA Molecules;" Inventor: Richard C. Conrad.

USPTO issued Office Action mailed Jun. 2, 2009 in U.S. Appl. No. 10/667,126, filed Sep. 19, 2003 entitled "Methods and Compositions for Isolating Small RNA Molecules;" Inventor: Richard C. Conrad.

International Search Report and Written Opinion mailed Dec. 28, 2004 for App No. PCT/US2004/023850 entitled "Methods and Compositions for Isolating Small RNA Molecules" Inventor: Conrad; Applicant: Ambion Inc.

International Preliminary Report on Patentability mailed Jan. 30, 2008 for App No. PCT/US2004/023850 entitled "Methods and Compositions for Isolating Small RNA Molecules" Inventor: Conrad; Applicant: Ambion Inc.

* cited by examiner

METHODS AND COMPOSITIONS FOR ISOLATING SMALL RNA MOLECULES

The present application is a continuation application of U.S. application Ser. No. 10/667,126 filed Sep. 19, 2003, which application claims the benefit of U.S. Provisional Application Ser. No. 60/490,325, filed on Jul. 25, 2003, which applications are incorporated by reference herein in their entirety.

BACKGROUND OF THE INVENTION

1. Field of the Invention

The present invention relates generally to the fields of molecular biology and biotechnology. More particularly, it concerns methods and compositions for isolating small RNA molecules that are typically 100 nucleotides or fewer, such as siRNA and miRNA, as opposed to larger RNA or DNA molecules. The isolated small RNA molecules can be used in subsequent studies or assays.

2. Description of Related Art

The study of small RNAs—RNA molecules on the order of 100 nucleotides or fewer—from various tissues in many organisms, as well as cultured cells, is an area of extreme interest now, and promises to remain one for the future. These small RNAs include microRNA molecules (miRNA) and small interfering RNA molecules (siRNA), both of which can have a powerful effect on the expression of a gene by virtue of hybridization to their target mRNA. Additionally, these procedures would be applicable to isolating small nuclear and small nucleolar RNAs (snRNAs and snoRNAs), involved in mRNA and rRNA processing. The procedures could also be used to isolate tRNAs along with 5S and 5.8S rRNAs, which are all involved in protein translation.

Key to these studies is the need to isolate RNA molecules in the size range of 15 to 100 nucleotides with high efficiency. Methods that provide a straightforward methodology to do this are therefore quite valuable.

The preparation of RNA from natural sources (tissue samples, whole organisms, cell cultures, bodily fluids) requires removal of all other biomolecules. Once water is eliminated, the primary component of cells is usually protein, often providing three-quarters of the mass. Of the major other biomolecules, lipids, carbohydrates, combinations of these with each other and protein, and DNA are the other main components. A goal of RNA extraction is to remove protein and DNA, as these provide the greatest interference in the use of RNA. Lipid and carbohydrate moieties can usually be dissolved away with the aid of a detergent. Protein can be stripped off RNA (and DNA) with the aid of detergents and denaturants, but still must be removed from the common solution.

Two main methods have historically been used to accomplish this end. The first is the use of organic solvents that are immiscible with water to dissolve (literally, to chemically extract) or precipitate proteins, after which the aqueous, protein-free phase can be separated by centrifugation prior to removal. Usually, phenol or phenol-chloroform mixtures are used for this purpose. The second method selectively immobilizes the RNA on a solid surface and rinses the protein away, after which conditions are used to release the RNA in an aqueous solution. This is literally a solid-phase extraction. Both procedures can reduce the amount of DNA contamination or carryover, with the efficiency varying with the precise conditions employed.

Phenol and phenol-chloroform extractions provide an extremely protein- and lipid-free solution of nucleic acid. Much if not all (depending on the sample) of the carbohydrate is also lost in this procedure as well. Acid phenol-chloroform is known to extract some of the DNA out of the aqueous solution (Chomczynski and Sacchi, 1987). However, the solution is high in denaturing agents such as guanidinium hydrochloride, guanidinium thiocyanate, or urea, all of which are incompatible with downstream enzymatic analysis, and the first two with electrophoretic analysis as well. RNA is usually separated from these mixtures by selective precipitation, usually with ethanol or isopropanol. This procedure is not as effective for small nucleic acid molecules, so this procedure is not ideal for the preparation of small RNAs.

Solid-phase extraction relies on high salt or salt and alcohol to decrease the affinity of RNA for water and increase it for the solid support used. The use of glass (silica) as a solid support has been shown to work for large RNAs in the presence of high concentrations of denaturing salts (U.S. Pat. Nos. 5,155,018; 5,990,302; 6,043,354; 6,110,363; 5,234,809; Boom et al., 1990) or lower concentrations of denaturing salts plus ethanol (U.S. Pat. No. 6,180,778). However, normal conditions for binding to glass fiber for RNA do not work for microRNA, and the use of a raw lysate is problematic due to variable requirements with different tissues.

Many of the protocols known involve isolation of DNA or larger mRNA, which are not ideal for isolation of small RNA molecules because these are often not effectively captured and eluted. Thus, there is a need for improved techniques for the efficient isolation, detection, and accurate quantification of these recently discovered small RNA molecules.

SUMMARY OF THE INVENTION

The present invention concerns methods and compositions for isolating, extracting, purifying, characterizing, quantifying, and/or assaying small RNA molecules from a sample, including a cell sample. Such compositions and methods allow for manipulation of small RNA molecules, which are often lost or depleted when methods for generally isolating larger RNA molecules are employed.

Thus, it is contemplated that the invention concerns small RNA molecules, which are, in most embodiments, understood to be RNA molecules of about 100 nucleotides or fewer. Small RNA molecules include siRNA and miRNA molecules. In some embodiments of the invention, the small RNA molecules have at most 100 nucleotides or fewer, have at most 70 nucleotides or fewer, or have at most 30 nucleotides or fewer, or have at most 25, 24, 23, 22, 21, 20, 19, 18, 17, 16, 15 nucleotides or fewer.

In some cases, the small RNA molecules are double stranded. In some cases, the small RNA molecules are single stranded, though they may have regions of self-complementarity. There may be 1, 2, 3, 4, 5, 6, 7, 8, 9, 10 or more such regions, and these regions may involve 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more basepairs (and thus, twice as many bases). Furthermore, these regions of complementarity may involve 100% complementarity or it may involve some mismatches, such as at least 70%, 75%, 80%, 85%, 90%, 95%, 96%, 97%, 98%, or 99% identity in the region among bases, or a region may contain 1, 2, 3, 4, 5, 6, 7, 8, 9 10 or more mismatches among bases in the region.

It is specifically contemplated that methods and compositions of the invention can be used to isolate small RNA molecules that are at most 100, 95, 90, 85, 80, 75, 70, 65, 60, 55, 50, 45, 40, 35, 30, 25, 24, 23, 22, 21, 20, 19, 18, 17, 16, 15, 10 or fewer nucleotides in length, and all ranges derivable between these integers. Furthermore, such molecules can be isolated so that a sample is enriched in the amount of small RNA molecules present.

There are several ways in which enrichment and/or purification of small RNAs may be expressed in the context of the invention. Any increase in the amount of small RNA molecules present in a sample is within the scope of the invention.

Enrichment and/or purification of small RNAs may be measured in terms of mass of small RNA relative to mass of total RNA. For example, small RNA in a sample may be enriched about or at least about 1×, 1.5×, 2×, 2.5×, 3×, 3.25×, 3.5×, 3.75×, 4×, 4.25×, 4.5×, 4.75×, 5×, 5.25×, 5.5×, 5.75×, 6×, 6.25×, 6.5×, 6.75×, 7×, 7.25×, 7.5×, 7.75×, 8×, 8.25×, 8.5×, 8.75×, 9×, 9.5×, 10×, 15×, 20×, 25×, 30×, 35×, 40×, 45×, 50×, 55×, 60×, 65×, 70×, 75×, 80×, 85×, 90×, 95×, 100×, 110×, 120×, 130×, 140×, 150×, 160×, 170×, 180×, 190×, 200×, 210×, 220×, 230×, 240×, 250×, 260×, 270×, 280×, 290×, 300×, 325×, 350×, 375×, 400×, 425×, 450×, 475×, 500×, 525×, 550×, 575×, 600×, 625×, 650×, 675×, 700×, 725×, 750×, 775×, 800×, 825×, 850×, 875×, 900×, 925×, 950×, 975×, 1000×, 1100×, 1200×, 1300×, 1400×, 1500×, 1600×, 1700×, 1800×, 1900×, 2000× (same as -fold), and all ranges derivable therein in small RNA molecules as determined by the mass of small RNA molecules relative to the mass of total RNA molecules prior to placing the lysate on the solid support compared to after eluting the RNA from the solid support.

Enrichment and/or may, alternatively, be measured in terms of the number of small RNA molecules relative to the number of total RNA molecules. Small RNA molecules can be isolated such that a sample is enriched about or at least about 2×, 3×, 4×, 5×, 10×, 15×, 20×, 25×, 30×, 35×, 40×, 45×, 50×, 55×, 60×, 65×, 70×, 75×, 80×, 85×, 90×, 95×, 100×, 110×, 120×, 130×, 140×, 150×, 160×, 170×, 180×, 190×, 200×, 210×, 220×, 230×, 240×, 250×, 260×, 270×, 280×, 290×, 300×, 325×, 350×, 375×, 400×, 425×, 450×, 475×, 500×, 525×, 550×, 575×, 600×, 625×, 650×, 675×, 700×, 725×, 750×, 775×, 800×, 825×, 850×, 875×, 900×, 925×, 950×, 975×, 1000×, 1100×, 1200×, 1300×, 1400×, 1500×, 1600×, 1700×, 1800×, 1900×, 2000× (same as -fold) and all ranges derivable therein in small RNA molecules as determined by number of small RNA molecules relative to number of RNA molecules prior to placing the lysate on the solid support compared to after eluting the RNA from the solid support.

Enrichment and/or purification of small RNAs may also be measured in terms of the increase of small RNA molecules relative to the number of total RNA molecules. Small RNA molecules can be isolated such that the amount of small RNA molecules is increased about or at least about 10%, 15%, 20%, 25%, 30%, 35%, 40%, 45%, 50%, 55%, 60%, 65%, 70%, 75%, 80%, 85%, 90%, 95% or more with respect to the total amount of RNA in the sample before and after isolation.

Alternatively, in some embodiments, the enrichment and/or purification of small RNA molecules can be quantified in terms of the absence of large RNA molecules present in the sample after eluting the RNA from the solid support. Small RNA molecules can be enriched such that the number of RNA molecules larger than 200 nucleotides by mass remaining in the sample after eluting the RNA from the solid support is no more than about 30%, 25%, 20%, 15%, 10%, 5%, 4%, 3%, 2%, 1%, 0.5%, 0%, or any range therein of the RNA eluted from the solid support.

In some embodiments, about or at least about 10%, 15%, 20%, 25%, 30%, 35%, 40%, 45%, 50%, 55%, 60%, 65%, 70%, 75%, 80%, 85%, 90%, 95% of the small RNA molecules in a sample is isolated after the method is implemented.

Methods of the invention include methods for efficiently isolating small RNA molecules from cells comprising: a) lysing the cells with a lysing solution to produce a lysate; b) adding an alcohol solution to the lysate; c) applying the lysate to a solid support; and d) eluting RNA molecules from the solid support.

Because the small RNA molecules are being efficiently isolated, methods of the invention include a step of e) using or characterizing the small RNA molecules. Using or characterizing the small RNA molecules is distinguished from discarding the small RNA molecules or having them as a byproduct or contaminant in a reaction or assay involving other types of molecules isolated from the sample, such as longer RNA molecules or DNA molecules.

Samples from which small RNA molecules may be isolated include any sample containing such molecules. The sample may be or contain cells, tissue, organs, or other biological sample. Alternatively, the sample may be a reaction mixture, such as one in which small RNA molecules were produced, generated, or created by enzymatic, synthetic, and/or recombinant means.

In some embodiments, methods of the invention involve lysing a sample that contains cells. A "lysate" results when a cell is lysed or its integrity disrupted. In specific embodiments of the invention, a lysing solution is implemented to lyse a cell sample, and the solution includes a chaotropic agent or detergent. A "chaotropic agent" refers to an agent that unfolds ordered macromolecules, thereby causing them to lose their function (hence causing binding proteins to release their target). A "detergent" refers to a substance that can disperse a hydrophobic substance (usually lipids) in water by emulsification. The concentration of a chaotropic agent in the solutions of the invention, particularly lysing solutions, is about, is at most about, or is at least about 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5 M or more, and ranges therein. In specific embodiments, the concentration of guanidinium in the lysing solution is between about 2.0 M and 4.0 M. In some embodiments, the chaotropic agent is guanidinium chloride or guanidinium isothiocyanate. In still further embodiments, the lysing solution also contains a detergent and/or buffer. The concentration of the detergent is between 0.1% to about 2% in some embodiments. The detergent, particularly a mild one that is nondenaturing, can act to solubilize the sample. Detergents may be ionic or nonionic. The ionic detergent N-lauroyl sarcosine is specifically contemplated for use in solutions of the invention. The concentration of the detergent in the buffer may be about, at least about, or at most about 0.05%, 0.06%, 0.07%, 0.08%, 0.09%, 0.1%, 0.2%, 0.3%, 0.4%, 0.5%, 0.6%, 0.7%, 0.8%, 0.9%, 1.0%, 1.5%, 2.0%, 2.5%, 3.0%, 3.5%, 4.0%, 4.5%, 5.0%, 5.5%, 6.0%, 6.5%, 7.0%, 7.5%, 8.0%, 8.5%, 9.0%, 9.5%, 10.0% or any range therein. It is contemplated that the concentration of the detergent can be up to an amount where the detergent remains soluble in the solution.

In other embodiments of the invention, there is a buffer in solutions of the invention, including a lysing solution. In specific embodiments, the buffer is at a concentration of about, at least about, or at most about 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 270, 275, 280, 285, 290, 295, 300, 310, 320, 330, 340, 350, 360, 370, 380, 390, 400, 410, 420, 430, 440, 450, 460, 470, 480, 490, 500 mM or any range therein in the solution or in the solution with the sample. In certain cases, the buffer concentration in the lysing solution is between about 10 mM and 300 mM. Moreover, in other embodiments, the buffer is TrisCl, although it is contemplated that other buffers may be employed as well.

An alcohol solution is added to, mixed with, or incubated with the lysate in embodiments of the invention. An alcohol solution is contemplated to contain at least one alcohol. The alcohol solution can be about, be at least about, or be at most about 5, 10, 15, 20, 25, 30, 35, 40, 45, 50, 55, 60, 65, 70, 75, 80, 85, 90, 95, or 100% alcohol, or any range therein. In certain embodiments, it is added to a lysate to make the lysate have a concentration of alcohol of about, about at least, or about at most 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, or 90%, or any range therein. In specific embodiments, the amount of alcohol added to a lysate renders it with an alcohol concentration of about 35% to about 70%, or about 50% to about 60%. In specific embodiments, the amount of alcohol solution added to the lysate gives it an alcohol concentration of 55%. Alcohols include, but are not limited to, ethanol, propanol, isopropanol, and methanol. Ethanol is specifically contemplated for use in aspects of the invention. It is further contemplated that an alcohol solution may be used in additional steps of methods of the invention to precipitate RNA.

It is contemplated that the pH of any solution, or of the buffer component of any solution, or of any solution with the sample is between about 4.5 and 10.5, though it can be about, about at least, or about at most 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.1, 10.2, 10.3, 10.4, 10.5 or any range therein.

Other methods of the invention also include extracting small RNA molecules from the lysate with an extraction solution comprising a non-alcohol organic solvent prior to applying the lysate to the solid support. In specific embodiments, the extraction solution contains a non-alcohol organic solvent such as phenol and/or chloroform. The non-alcohol organic solvent solution is understood to contain at least one non-alcohol organic solvent, though it may also contain an alcohol. The concentrations described above with respect to alcohol solutions are applicable to concentrations of solutions having non-alcohol organic solvents. In specific embodiments, equal amounts of 1) the lysate and 2) phenol and/or chloroform are mixed. In specific embodiments, the alcohol solution is added to the lysate before extraction with a non-alcohol organic solvent.

Extraction of RNA from the lysate includes using a solid support, such as a mineral or polymer support. A "solid support" refers to a physical structure containing a material which contacts the lysate and that does not irreversibly react to macromolecules in the lysate, particularly with small RNA molecules In particular embodiments, the solid support binds small RNA molecules; in additional cases, it binds small RNA molecules, but does not bind one or more other types of macromolecules in the sample. The material in the solid support may include a mineral or polymer, in which case the support is referred to as a "mineral or polymer support." Mineral or polymer supports include supports involving silica. In some embodiments, the silica is glass. Supports include, but are not limited to, beads, columns and filters. In further embodiments, the mineral or polymer support is a glass fiber filter or column.

Alternatively, in some embodiments, the mineral or polymer support may include polymers or nonpolymers with electronegative groups. In some embodiments, the material is or has polyacrylate, polystyrene, latex, polyacrylonitrile, polyvinylchloride, methacrylate, and/or methyl methacrylate. Such supports are specifically contemplated for use with the present invention.

In some methods of the invention, a lysate that may or may not have been mixed with an alcohol or non-alcohol organic solvent solution is applied to a solid support and the RNA is eluted from the support.

After a lysate is applied or mixed with a solid support, the material may be washed with a solution. In some embodiments, a mineral or polymer support is washed with a first wash solution after applying the lysate to the mineral or polymer support. In further embodiments, a wash solution comprises a chaotropic or reducing agent. The chaotropic agent is guanidinium in some wash solutions. A wash solution includes alcohol in some embodiments of the invention, and in some cases, it has both alcohol and guanidinium. It is further contemplated that methods of the invention involve 1, 2, 3, 4, 5 or more washes with a wash solution. The wash solution used when more than one washing is involved may be the same or different. In some embodiments, the wash solutions have the same components but in different concentrations from each other. It is generally understood that molecules that come through the material in a wash cycle are discarded.

In other methods of the invention, the desired RNA molecules are eluted from the solid support. In certain embodiments, small RNA molecules are eluted from a solid support such as a mineral or polymer support at a temperature of about 60° C. to about 100° C. It is contemplated that the temperature at which the RNA molecules are eluted is about or at least about 5, 10, 15, 20, 25, 30, 35, 40, 45, 50, 55, 60, 65, 70, 75, 80, 85, 90, 95, 100° C. or more, or any range therein. The molecules may be eluted with any elution solution. In some embodiments, the elution solution is an ionic solution, that is, it includes ions. In particular embodiments, the elution solution includes up to 10 mM salt. It is contemplated to be about, at least about, or at most about 0.1, 0.5, 1, 2, 3, 4, 5, 6, 7, 8, 9, 10 or more mM salt. In certain embodiments, the salt consists of a combination of $Li^+$, $Na^+$, $K^+$, or $NH_4^+$ as cation and $Cl^-$, $Br^-$, $I^-$, ethylenediaminetetraacetate, or citrate as anion.

Additional method steps include passing the small RNA molecules through a GFF while binding only the larger RNAs. In some embodiments, the passed small RNA molecules are captured on a second GFF and then eluted. Material that is not captured on the second GFF filter is discarded or not used in additional methods of the invention.

Specific methods of the invention concern isolating miRNA or siRNA from a sample by at least the following steps: a) obtaining a sample having miRNA or siRNA; b) adding an extraction solution to the sample; c) adding an alcohol solution to the extracted sample; d) applying the sample to a mineral or polymer support; and, e) eluting the RNA containing siRNA or miRNA from the mineral or polymer support with an ionic solution. In particular embodiments, the sample is a cell lysate. The cell lysate, in some cases, is produced by adding a lysing solution comprising a chaotropic agent or detergent to cells having miRNA or siRNA. In some embodiments, the eluted sample is enriched at least about 10-fold for miRNA and/or siRNA by mass.

Additional methods for isolating miRNA molecules from a sample involve: a) adding an alcohol solution to the sample; b) applying the sample to a mineral or polymer solid support; c) eluting miRNA molecules from the support with an ionic solution; and, d) using or characterizing the miRNA molecules.

Other methods for isolating small RNA molecules from a sample include: a) lysing cells in the sample with a lysing solution comprising guanidinium, wherein a lysate with a concentration of at least about 1 M guanidinium is produced; b) extracting small RNA molecules from the lysate with an extraction solution comprising phenol; c) adding to the lysate an alcohol solution for form a lysate/alcohol mixture, wherein the concentration of alcohol in the mixture is between about 35% to about 70%; d) applying the lysate/alcohol mixture to a solid support; e) eluting the small RNA molecules from the solid support with an ionic solution; f) capturing the small RNA molecules; and, g) using the isolated small RNA molecules.

After RNA is extracted, individual or specific RNA molecules and/or pools of RNA molecules (as well as the entire population of isolated RNA) can be subject to additional reactions and/or assays. In some cases, these reactions and/or assays involve amplification of the RNA or of a DNA molecule generated from the RNA. For example, RT-PCR may be employed to generate molecules that can be characterized.

In some embodiments, a particular RNA molecule or an RNA population may be quantified or characterized. Quantification includes any procedure known to those of skill in the art such as those involving one or more amplification reactions or nuclease protection assays, such as those using ribonuclease to discriminate between probe that is hybridized to a specific miRNA target or unhybridized, as embodied in the mirVana miRNA Detection Kit from Ambion. These procedures include quantitative reverse transcriptase-PCR (qRT-PCR). In some embodiments, characterization of the isolated RNA is performed. cDNA molecules are generated from the extracted RNA. Other characterization and quantification assays are contemplated as part of the invention. The methods and compositions of the invention allow small RNA molecules to be quantified and characterized. The small RNA molecules can also be used with arrays; to generate cDNAs for use in arrays or as targets to be detected by arrays, after being labeled by radioactive, fluorescent, or luminescent tags. Other assays include the use of spectrophotometry, electrophoresis, and sequencing.

The present invention also concerns kits for isolating small RNA molecules, such as miRNA and/or siRNA from a sample, particularly a cell sample. Thus, any of the compositions discussed above can be included with any other composition discussed above for inclusion in a kit. In some embodiments, there are kits for isolating small RNA molecules comprising: a) acid phenol-chloroform; b) a lysis/binding buffer, c) a small RNA homogenate additive, d) one or more small RNA wash solution(s), and e) an elution solution.

In preferred embodiment, the kit contains: a) an acid phenol-chloroform; b) a lysis/binding buffer comprising 4 M GuSCN, 0.1 M beta-mercaptoethanol, 0.5% N-lauroyl sarcosine, 25 mM Na-citrate, pH 7.2; c) a small RNA homogenate additive comprising 2 M sodium acetate, pH 4, to be added in 0.1 volume before extraction with PC; d) a wash solution #1 comprising 1.6 M GuSCN in 70% ethanol; e) a wash solution #2/3 comprising 80% ethanol, 0.1 M NaCl, 4.5 mM EDTA, 10 mM TrisHCl, pH 7.5; f) an elution solution comprising 0.1 mM EDTA, pH8; g) a gel loading buffer II; h) collection tubes; and i) filter cartridges.

In some embodiments, kits of the invention include one or more of the following in a suitable container means (consistent with compositions discussed above): a lysis buffer with a chaotropic agent; a glass fiber filter or column; elution buffer; wash buffer; alcohol solution; and RNase inhibitor.

The components of the kits may be packaged either in aqueous media or in lyophilized form. The container means of the kits will generally include at least one vial, test tube, flask, bottle, syringe or other container means, into which a component may be placed, and preferably, suitably aliquoted. Where there are more than one component in the kit (they may be packaged together), the kit also will generally contain a second, third or other additional container into which the additional components may be separately placed. However, various combinations of components may be comprised in a vial. The kits of the present invention also will typically include a means for containing the RNA, and any other reagent containers in close confinement for commercial sale. Such containers may include injection or blow-molded plastic containers into which the desired vials are retained. When the components of the kit are provided in one and/or more liquid solutions, the liquid solution is an aqueous solution, with a sterile aqueous solution being particularly preferred.

However, the components of the kit may be provided as dried powder(s). When reagents and/or components are provided as a dry powder, the powder can be reconstituted by the addition of a suitable solvent. It is envisioned that the solvent may also be provided in another container means. The container means will generally include at least one vial, test tube, flask, bottle, syringe and/or other container means, into which the nucleic acid formulations are placed, preferably, suitably allocated. The kits may also comprise a second container means for containing a sterile, pharmaceutically acceptable buffer and/or other diluent.

Such kits may also include components that preserve or maintain the RNA or that protect against its degradation. Such components may be RNAse-free or protect against RNAses. Such kits generally will comprise, in suitable means, distinct containers for each individual reagent or solution.

It is contemplated that any embodiment discussed herein can be implemented with respect to any method or composition of the invention, and vice versa. Furthermore, compositions and kits of the invention can be used to achieve methods of the invention.

The use of the term "or" in the claims is used to mean "and/or" unless explicitly indicated to refer to alternatives only or the alternatives are mutually exclusive, although the disclosure supports a definition that refers to only alternatives and "and/or."

Throughout this application, the term "about" is used to indicate that a value includes the standard deviation of error for the device or method being employed to determine the value.

Following long-standing patent law, the words "a" and "an," when used in conjunction with the word "comprising" in the claims or specification, denotes one or more, unless specifically noted.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

I. Small RNA Molecules

Figure 1:
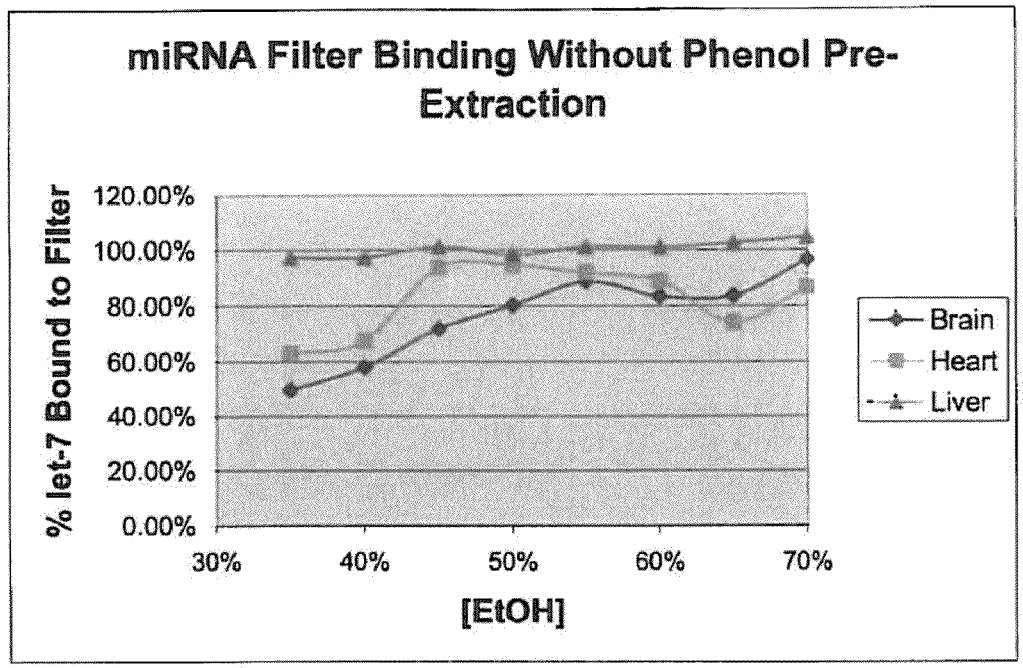
FIG. 1. Binding behavior of let-7 miRNA in raw extracts from mouse brain, heart, and liver at various ethanol concentrations. Absolute ethanol was added to crude lysate to create the final ethanol concentrations indicated.

Natural populations of RNA are routinely isolated from animal and plant tissue as well as cells grown in culture. However, most of these procedures are unconcerned with retaining small RNAs, in the range of less than 100 nucleotides long. In fact, it is known that standard precipitation procedures with alcohol are inefficient in capturing nucleic acids smaller than around 100 nucleotides.

The presence of small RNA molecules and free nucleotides has long been observed in RNA extracted from biological samples and assumed to reflect the breakdown products of larger protein-coding and functional RNAs, including those involved in translation and RNA processing complexes. In the past few years, small RNAs involved in the regulation of gene expression have been found to be present in virtually all eukaryotic organisms. In 1993, the Ambrose lab published a report on the discovery that the let-7gene, which results in developmental mis-timing, or heterochromy, in the nematode *Caenorhabditis elegans* coded for a 22-nt RNA (Lee et al., 1993.). This small, single-stranded RNA (now termed microRNA or miRNA) affects the expression of a set of developmental genes by inhibiting their ability to function in translation based on partial sequence complementarity with the targeted gene. The presence of this small RNA was found to be conserved in many evolutionarily divergent species (Pasquinelli et al., 2000), including vertebrate, ascidian, hemichordate, mollusc, annelid and arthropod.

In 2001, several groups used a novel cloning method to isolate and identify a large variety of these "micro RNAs" (miRNAs) from *C. elegans, Drosophila*, and humans (Lagos-Quintana et al., 2001; Lau et al., 2001; Lee and Ambros, 2001). Several hundreds of miRNAs have been identified in plants and animals.

miRNAs thus far observed have been approximately 21-22 nucleotides in length and they arise from longer precursors, which are transcribed from non-protein-encoding genes. See review of Carrington et al. (2003). The precursors form structures that fold back on each other in self-complementary regions; they are then processed by the nuclease Dicer in animals or DCL1 in plants. miRNA molecules interrupt translation through imprecise base-pairing with their targets.

Micro RNAs are not the only RNAs of that size found in eukaryotic cells. A pathway for degradation of mRNAs in the cell was found that creates small double-stranded RNAs (Fire et al., 1998; Zamore et al., 2000; many others, reviewed in Timmons, 2002.). This process, called RNA interference, uses these "small interfering RNAs" (siRNAs) to target their degradation sites, usually from a much larger double-stranded intermediate. Although the natural function of this system is not known, it is thought to be involved in the response to infective agents. Plants have been found to have a similar system, which also utilizes microRNAs in post-transcriptional gene-silencing (Hamilton and Baulcombe, 1999; Tang et al. 2003).

II. Isolation of Short RNA Molecules

Methods of the invention involve one or more steps to efficiently isolate and/or enrich short RNA molecules. These steps include or involve the following: lysing cells and/or creating a cell lysate;

A. Creating Cell Lysates

It is contemplated that the present invention can be used to facilitate preparation of small RNA molecules from biological samples for evaluation and subsequent use. In some embodiments of the invention, preparation of samples involves homogenizing the sample or preparing a cell lysate from the sample. In embodiments of the invention, homogenization or lysing of a cell is accomplished using a solution that contains a guanidinium salt, detergent, surfactant, or other denaturant. The terms homogenization and lysing are used interchangeably.

Guanidinium salts are well known to those of skill in the art and include guanidinium hydrochloride and guanidinium isothiocyanate. In some embodiments, they may be present in a concentration of about 2 to about 5 M. Additionally, a homogenization solution may contain urea or other denaturants such as NaI.

In embodiments of the invention, a buffer is included in the lysis or homogenization solution. In certain cases, the buffer is TrisCl.

A biological sample may be homogenized or fractionated in the presence of a detergent or surfactant. The detergent can act to solublize the sample. Detergents may be ionic or nonionic. Examples of nonionic detergents include triton, such as the Triton X series (Triton X-100, Triton X-100R, Triton X-114, Triton X-450, Triton X-450R), octyl glucoside, polyoxyethylene(9)dodecyl ether, digitonin, IGEPAL CA630, n-octyl-beta-D-glucopyranoside (betaOG), n-dodecyl-beta, C12EO7, Tween 20, Tween 80, polidocanol, n-dodecyl beta-D-maltoside (DDM), NP-40, C12E8 (octaethylene glycol n-dodecyl monoether), hexaethyleneglycol mono-n-tetradecyl ether (C14EO6), octyl-beta-thioglucopyranoside (octyl thioglucoside, OTG), Emulgen, and polyoxyethylene 10 lauryl ether (C12E10). Examples of ionic detergents (anionic or cationic) include deoxycholate, sodium dodecyl sulfate (SDS), N-lauroylsarcosine, and cetyltrimethylammonium-bromide (CTAB). A zwitterionic reagent may also be used in the purification schemes of the present invention, such as Chaps, zwitterion 3-14, and 3-[(3-cholamidopropyl)dimethylammonio]-1-propanesulfonate. It is contemplated also that urea may be added with or without another detergent or surfactant.

Lysis or homogenization solutions may further contain other agents such as reducing agents. Examples of such reducing agents include dithiothreitol (DTT), β-mercaptoethanol, DTE, GSH, cysteine, cysteamine, tricarboxyethyl phosphine (TCEP), or salts of sulfurous acid.

In some embodiments of the invention, a lysis solution includes: guanidinium thiocyanate, N-lauroyl sarcosine, and TrisHCl. Once the sample has been homogenized into this solution, the RNA can be extracted, often with phenol solutions or the use of an adsorptive solid phase. Alternative methods use combination denaturant/phenol solutions to perform the initial homogenization, precluding the need for a secondary extraction. Examples of these reagents would be Trizol™ (Invitrogen) or RNAwiz™ (Ambion, Inc.)

Subsequent to exposure to a homogenization solution, samples may be further homogenized by mechanical means. Mechanical blenders, rotor-stator homogenizers, or shear-type homogenizers may be employed.

Alternatively, the tissue could be homogenized in the lysis solution, and the tissue remains separated by settling, centrifugation, or filtration. These remains could then be treated with homogenization solution and extraction conditions as described above.

The methods of the invention may further include steps involving removing lipids or compositions thereof with detergents or surfactants. A lipid may be naturally occurring or synthetic (i.e., designed or produced by man). However, a lipid is usually a biological substance. Biological lipids are well known in the art, and include for example, neutral fats, phospholipids, phosphoglycerides, steroids, terpenes, lysolipids, glycosphingolipids, glucolipids, sulphatides, lipids with ether and ester-linked fatty acids and polymerizable lipids, and combinations thereof. Removal of a lipid such as a phospholipid is described herein.

Detergents may be used to facilitate homogenization or the creation of a cell lysate. These detergents specifically include Triton X-100 and CHAPS. CHAPS is the zwitterionic detergent 3-[(3-cholamidopropyl)-dimethyl-ammonio]-1-propanesulfonate.

B. Extracting Small RNA Molecules

After lysing or homogenizing a cell sample, additional procedures may be implemented to extract specifically RNA molecules. It is contemplated that if the sample involves cells, the step of lysing or homogenizing can be considered part of an overall extraction process, however, the extraction of RNA specifically may be referred to, and will be understood as separating RNA molecules from other biomolecules such as lipids and proteins. Extraction of RNA molecules from these other structures can involve extraction solutions containing one or more organic solvents. In some cases, the organic solvent is a non-alcohol organic solvent such as phenol and/or chloroform. In others, a solution contains an alcohol, which may be any alcohol used for the extraction of nucleic acids, but in certain embodiments, the alcohol is ethanol.

RNA molecules may be extracted from a variety of cell samples. Such cell samples may comprise cells of the brain, head, neck, gastrointestinal tract, lung, liver, pancreas, breast, testis, uterus, bladder, kidney, prostate, colon, kidney, skin, ovary, and heart but is not limited to such cells.

The term "nucleic acid" is well known in the art. A "nucleic acid" as used herein will generally refer to a molecule (i.e., a strand) of DNA, RNA or a derivative or analog thereof, comprising a nucleobase. A nucleobase includes, for example, a naturally occurring purine or pyrimidine base found in DNA (e.g., an adenine "A," a guanine "G," a thymine "T" or a cytosine "C") or RNA (e.g., an A, a G, an uracil "U" or a C). The term "nucleic acid" or "RNA molecule" encompasses the terms "oligonucleotide" and "polynucleotide," each as a sub-genus of the term "nucleic acid."

A nucleic acid "complement(s)" or is "complementary" to another nucleic acid when it is capable of base-pairing with another nucleic acid according to the standard Watson-Crick, Hoogsteen or reverse Hoogsteen binding complementarity rules. As used herein "another nucleic acid" may refer to a separate molecule or a spatial separated sequence of the same molecule.

As used herein, the term "complementary" or "complement(s)" also refers to a nucleic acid comprising a sequence of consecutive nucleobases or semi-consecutive nucleobases (e.g., one or more nucleobase moieties are not present in the molecule) capable of hybridizing to another nucleic acid strand or duplex even if less than all the nucleobases do not base pair with a counterpart nucleobase. In certain embodiments, a "complementary" nucleic acid comprises a sequence in which about 70%, about 71%, about 72%, about 73%, about 74%, about 75%, about 76%, about 77%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, to about 100%, and any range derivable therein, of the nucleobase sequence is capable of base-pairing with a single or double stranded nucleic acid molecule during hybridization. In certain embodiments, the term "complementary" refers to a nucleic acid that may hybridize to another nucleic acid strand or duplex in stringent conditions, as would be understood by one of ordinary skill in the art.

In certain embodiments, a "partly complementary" nucleic acid comprises a sequence that may hybridize in low stringency conditions to a single or double stranded nucleic acid, or contains a sequence in which less than about 70% of the nucleobase sequence is capable of base-pairing with a single or double stranded nucleic acid molecule during hybridization.

These definitions generally refer to a single-stranded molecule, but in specific embodiments will also encompass an additional strand that is partially, substantially or fully complementary to the single-stranded molecule. Thus, a nucleic acid may encompass a double-stranded molecule or a triple-stranded molecule that comprises one or more complementary strand(s) or "complement(s)" of a particular sequence comprising a molecule. As used herein, a single stranded nucleic acid may be denoted by the prefix "ss," a double stranded nucleic acid by the prefix "ds," and a triple stranded nucleic acid by the prefix "ts."

C. Solid Support and Devices

A solid support is a structure containing material that will reversibly bind with nucleic acids, particularly small RNA molecules, and in some embodiments, it will not bind one or more other types of macromolecules in the sample. Material may comprise plastic, glass, silica, a magnet, a metal such as gold, carbon, cellulose, latex, polystyrene, and other synthetic polymers, nylon, cellulose, nitrocellulose, polyacrylate, polyacrylonitrile, methacrylate, and/or methyl methacrylate polymethacrylate, polyvinylchloride, styrenedivinylbenzene, or any chemically-modified plastic. They may also be porous or non-porous materials. The structure may also be a particle of any shape that allows the small RNA molecules to be isolated, depleted, or separated. In some embodiments, it is a column that includes any of the materials described above through which a lysate may be passed.

Other components include isolation apparatuses such as filtration devices, including spin filters or spin columns. It may be a sphere, such as a bead, or a rod, or a flat-shaped structure, such as a plate with wells. The structure and sample containing the desired RNA molecules may be centrifuged, filtered, dialyzed, and/or otherwise isolated. When the structure is centrifuged it may be pelleted or passed through a centrifugible filter apparatus.

The structure may also go through an additional capture step. In some embodiments, the sample is subsequently filtered after passage through a capture structure. The capture step can include filtration using a pressure-driven system or gravity-based system (for example, centrifugation). Many such structures are available commercially and may be utilized herewith. Other examples can be found in WO 86/05815, WO90/06045, U.S. Pat. No. 5,945,525, all of which are specifically incorporated by reference.

II. Characterization and Quantitation of Isolated Small RNA Molecules

Small RNA molecules obtained from samples may be analyzed or quantitated by various methods to characterize them, quantitate them, or use them for analysis of other biological samples. Provided herein are methods of quantitating or analyzing RNA, or manipulating the RNA for use in assays involving other biological material. General methods for quantitating or analyzing RNA may be found in Sambrook et al. (2001) or Maniatis et al. (1990). Below are provides examples of for using small RNA molecules from samples, however, these examples and are not meant to be limiting.

A. Nuclease Protection Assays

Nuclease protection assays (NPAs), including both ribonuclease protection assays (RPAs) and S1 nuclease assays, are an extremely sensitive method for the detection, quantitation and mapping of specific RNAs in a complex mixture of total cellular RNA. The basis of NPAs is a solution hybridization of a single-stranded, discrete sized antisense probe(s) to an RNA sample. The small volume solution hybridization is far more efficient than more common membrane-based hybridization, and can accommodate up to 100 µg of total or poly(A) RNA. After hybridization, any remaining unhybridized probe and sample RNA are removed by digestion with a mixture of nucleases. Then, in a single step reaction, the nucleases are inactivated and the remaining probe:target hybrids are precipitated. These products are separated on a denaturing polyacrylamide gel and are visualized by autoradiography. If nonisotopic probes are used, samples are visualized by transferring the gel to a membrane and performing secondary detection.

Such techniques are well known to those of ordinary skill in the art. Commercial kits for such assays are readily available, such as the Direct Protect™ Lysate RPA Kit, Hyb-Speed™ RPA Kit, and RPA II and RPA III™ Ribonuclease Protection Assay Kits from Ambion.

B. Denaturing Agarose Gel Electrophoresis

Small RNA molecules isolated from a sample may be quantitated by gel electrophoresis using a denaturing gel system. Acrylamide gels are the preferred matrix for separations of this size, although high concentrations (~4%+) of modified agarose such as NuSieve (FMC, 191 Thomaston St., Rockland, Me. 04841) can also be used. A positive control should be included on the gel so that any unusual results can be attributed to a problem with the gel or a problem with the RNA under analysis. RNA molecular weight markers, an RNA sample known to be intact, or both, can be used for this purpose. It is also a good idea to include a sample of the starting RNA that was used in the enrichment procedure. The presence of specific small RNAs can be determined by blotting the contents of these gels onto hybridization membranes and probing with radioactive oligonucleotide (RNA or DNA-based) probes.

C. Assessing RNA Yield by UV Absorbence

The concentration and purity of RNA can be determined by diluting an aliquot of the preparation (usually a 1:50 to 1:100 dilution) in TE (10 mM Tris-HCl pH 8, 1 mM EDTA) or water, and reading the absorbence in a spectrophotometer at 260 nm and 280 nm.

An $A_{260}$ of 1 is equivalent to 40 µg RNA/ml. The concentration (µg/ml) of RNA is therefore calculated by multiplying the $A_{260}$×dilution factor×40 µg/ml. The following is a typical example:

The typical yield from 10 µg total RNA is 3-5 µg. If the sample is re-suspended in 25 µl, this means that the concentration will vary between 120 ng/µl and 200 ng/µl. One µl of the prep is diluted 1:50 into 49 µl of TE. The $A_{260}$=0.1. RNA concentration=0.1×50×40 µg/ml=200 µg/ml or 0.2 µg/µl. Since there are 24 µl of the prep remaining after using 1 µl to measure the concentration, the total amount of remaining RNA is 24 µl×0.2=4.8 µg.

D. Other Uses of Small RNA Molecules from Samples

Small RNA molecules obtained from a sample may be analyzed by or used in microarray technology. For example an arrays such as a gene array are solid supports upon which a collection of gene-specific probes has been spotted at defined locations. The probes localize complementary labeled targets from a nucleic acid sample, such as an RNA sample, population via hybridization. One of the most common uses for gene arrays is the comparison of the global expression patterns of an RNA population. Typically, RNA isolated from two or more tissue samples may be used. The RNAs are reverse transcribed using labeled nucleotides and target specific, oligodT, or random-sequence primers to create labeled cDNA populations. The cDNAs are denatured from the template RNA and hybridized to identical arrays. The hybridized signal on each array is detected and quantified. The signal emitting from each gene-specific spot is compared between the populations. Genes expressed at different levels in the samples generate different amounts of labeled cDNA and this results in spots on the array with different amounts of signal.

The direct conversion of RNA populations to labeled cDNAs is widely used because it is simple and largely unaffected by enzymatic bias. However, direct labeling requires large quantities of RNA to create enough labeled product for moderately rare targets to be detected by array analysis. Most array protocols recommend that 2.5 g of polyA or 50 g of total RNA be used for reverse transcription (Duggan, 1999). For practitioners unable to isolate this much RNA from their samples, global amplification procedures have been used.

The most often cited of these global amplification schemes is antisense RNA (aRNA) amplification (U.S. Pat. Nos. 5,514,545 and 5,545,522). Antisense RNA amplification involves reverse transcribing RNA samples with an oligo-dT primer that has a transcription promoter such as the T7 RNA polymerase consensus promoter sequence at its 5' end. First strand reverse transcription creates single-stranded cDNA. Following first strand cDNA synthesis, the template RNA that is hybridized to the cDNA is partially degraded creating RNA primers. The RNA primers are then extended to create double-stranded DNAs possessing transcription promoters. The population is transcribed with an appropriate RNA polymerase to create an RNA population possessing sequence from the cDNA. Because transcription results in tens to thousands of RNAs being created from each DNA template, substantive amplification can be achieved. The RNAs can be labeled during transcription and used directly for array analysis, or unlabeled aRNA can be reverse transcribed with labeled dNTPs to create a cDNA population for array hybridization. In either case, the detection and analysis of labeled targets are well known in the art. Other methods of amplification that may be employed include, but are not limited to, polymerase chain reaction (referred to as PCR™; see U.S. Pat. Nos. 4,683,195, 4,683,202 and 4,800,159, and Innis et al., 1988); and ligase chain reaction ("LCR"), disclosed in European Application No. 320 308, U.S. Pat. Nos. 4,883,750, 5,912,148. Qbeta Replicase, described in PCT Application No. PCT/US87/00880, may also be used as an amplification method Alternative methods for amplification of a nucleic acid such as RNA are disclosed in U.S. Pat. Nos. 5,843,650, 5,846,709, 5,846,783, 5,849,546, 5,849,497, 5,849,547, 5,858,652, 5,866,366, 5,916,776, 5,922,574, 5,928,905, 5,928,906, 5,932,451, 5,935,825, 5,939,291, 5,916,779 and 5,942,391, GB Application No. 2 202 328, and in PCT Application No. PCT/US89/01025, PCT Application WO 89/06700, PCT Application WO 88/10315, European Application No. 329 822, Kwoh et al., 1989; Frohman, 1994; Ohara et al., 1989; and Walker et al., 1992 each of which is incorporated herein by reference in its entirety.

cDNA libraries may also be constructed and used to analyze to the RNA extracted from a sample. Construction of such libraries and analysis of RNA using such libraries may be found in Sambrook et al. (2001); Maniatis et al. (1990); Efstratiadis et al. (1976); Higuchi et al. (1976); Maniatis et al. (1976); Land et al. (1981); Okayama et al. (1982); Gubler et al. (1983); Ko (1990); Patanjali et al. (1991); U.S. Patent Appln. 20030104468, each incorporated herein by reference.

The present methods and kits may be employed for high volume screening. A library of RNA or DNA can be created using methods and compositions of the invention. This library may then be used in high throughput assays, including microarrays. Specifically contemplated by the present inventors are chip-based nucleic acid technologies such as those described by Hacia et al. (1996) and Shoemaker et al. (1996). Briefly, these techniques involve quantitative methods for analyzing large numbers of genes rapidly and accurately. By using fixed probe arrays, one can employ chip technology to segregate target molecules as high density arrays and screen these molecules on the basis of hybridization (see also, Pease et al., 1994; and Fodor et al, 1991). The term "array" as used herein refers to a systematic arrangement of nucleic acid. For example, a nucleic acid population that is representative of a desired source (e.g., human adult brain) is divided up into the minimum number of pools in which a desired screening procedure can be utilized to detect or deplete a target gene and which can be distributed into a single multi-well plate. Arrays may be of an aqueous suspension of a nucleic acid population obtainable from a desired mRNA source, comprising: a multi-well plate containing a plurality of individual wells, each individual well containing an aqueous suspension of a different content of a nucleic acid population. Examples of arrays, their uses, and implementation of them can be found in U.S. Pat. Nos. 6,329,209, 6,329,140, 6,324,479, 6,322,971, 6,316,193, 6,309,823, 5,412,087, 5,445,934, and 5,744,305, which are herein incorporated by reference.

Microarrays are known in the art and consist of a surface to which probes that correspond in sequence to gene products (e.g., cDNAs, mRNAs, cRNAs, polypeptides, and fragments thereof), can be specifically hybridized or bound at a known position. In one embodiment, the microarray is an array (i.e., a matrix) in which each position represents a discrete binding site for a product encoded by a gene (e.g., a protein or RNA), and in which binding sites are present for products of most or almost all of the genes in the organism's genome. In a preferred embodiment, the "binding site" (hereinafter, "site") is a nucleic acid or nucleic acid analogue to which a particular cognate cDNA can specifically hybridize. The nucleic acid or analogue of the binding site can be, e.g., a synthetic oligomer, a full-length cDNA, a less-than full length cDNA, or a gene fragment.

The nucleic acid or analogue are attached to a solid support, which may be made from glass, plastic (e.g., polypropylene, nylon), polyacrylamide, nitrocellulose, or other materials. A preferred method for attaching the nucleic acids to a surface is by printing on glass plates, as is described generally by Schena et al., 1995a. See also DeRisi et al., 1996; Shalon et al., 1996. Other methods for making microarrays, e.g., by masking (Maskos et al., 1992), may also be used. In principal, any type of array, for example, dot blots on a nylon hybridization membrane (see Sambrook et al., 2001, which is incorporated in its entirety for all purposes), could be used, although, as will be recognized by those of skill in the art, very small arrays will be preferred because hybridization volumes will be smaller.

Use of a biochip is also contemplated, which involves the hybridization of a labeled molecule or pool of molecules to the targets immobilized on the biochip.

III. Kits

In further embodiments of the invention, there is a provided a kit for the isolation of small RNA molecules, such as miRNA and siRNA from a sample, particularly a cell sample. Any of the compositions described herein may be comprised in a kit. In a non-limiting example, reagents for lysing cells, extracting RNA the cell lysate, and/or analyzing or quantitating the RNA obtained may be included in a kit. The kits will thus comprise, in suitable container means, any of the reagents disclosed herein. It may also include one or more buffers or solutions, such as lysis buffer, extraction buffer, solutions to have alcohol added, elution solution, wash solution and other components for isolating the desired RNA, such as a capture structure. In some embodiments, there are kits for isolating small RNA molecules comprising: a) Acid Phenol-Chloroform; b) Lysis/Binding Buffer (GuSCN-based); c) miRNA Homogenate Additive (2M Sodium Acetate, pH 4, to be added in 0.1 vol before extraction with PC); d) miRNA Wash Soln #1 (1.6M GuSCN in 70% ethanol); e) Wash Soln #2/3 (80% ethanol, 0.1 M NaCl, 4.5 mM EDTA, 10 mM TrisHCl, pH 7.5); f) Elution Solution (0.1 mM EDTA, pH8); g) Gel Loading Buffer II; h) Collection Tubes; i) Filter Cartridges.

The components of the kits may be packaged either in aqueous media or in lyophilized form. The container means of the kits will generally include at least one vial, test tube, flask, bottle, syringe or other container means, into which a component may be placed, and preferably, suitably aliquoted. Where there are more than one component in the kit (they may be packaged together), the kit also will generally contain a second, third or other additional container into which the additional components may be separately placed. However, various combinations of components may be comprised in a vial. The kits of the present invention also will typically include a means for containing the RNA, and any other reagent containers in close confinement for commercial sale. Such containers may include injection or blow-molded plastic containers into which the desired vials are retained. When the components of the kit are provided in one and/or more liquid solutions, the liquid solution is an aqueous solution, with a sterile aqueous solution being particularly preferred.

However, the components of the kit may be provided as dried powder(s). When reagents and/or components are provided as a dry powder, the powder can be reconstituted by the addition of a suitable solvent. It is envisioned that the solvent may also be provided in another container means. The container means will generally include at least one vial, test tube, flask, bottle, syringe and/or other container means, into which the nucleic acid formulations are placed, preferably, suitably allocated. The kits may also comprise a second container means for containing a sterile, pharmaceutically acceptable buffer and/or other diluent.

Such kits may also include components that preserve or maintain the RNA or that protect against its degradation. Such components may be RNAse-free or protect against RNAses. Such kits generally will comprise, in suitable means, distinct containers for each individual reagent or solution.

A kit will also include instructions for employing the kit components as well the use of any other reagent not included in the kit. Instructions may include variations that can be implemented.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Preparation of Cell Lysate and Isolation of RNA

The following procedure provides the basis for the invention and is referred to in the Examples as the Ambion miRNA Isolation Kit (AMIK) procedure.

Frozen tissue was ground under liquid nitrogen to a fine powder. Lysis buffer (4 M GuSCN; 0.1 M beta-mercaptoethanol; 0.5% N-lauroyl sarcosine; 25 mM Na-citrate, pH 7.2) was added to this powder in an appropriate vessel at a proportion of 1 ml to every gram of tissue powder. This was homogenized using mechanical means to create a finely-dispersed tissue lysate. One tenth volume of a 2 M Na acetate (pH 4.0) solution was added and mixed thoroughly, adding 0.1 ml for every ml. The lysate was then processed immediately (without organic extraction) or placed on ice to be processed within 15 minutes.

Processing involved the addition of an equal volume of Acid Phenol-Chloroform (5:1, equilibrated with aqueous solution at pH 4.5) to the suspension, followed by vigorous agitation (by vortexing or shaking) for 30-60 sec. The phenol-chloroform and aqueous phases were then separated by centrifugation at 16,000×G for 5 min, or until a clear interface was obtained. The aqueous phase was removed by aspiration, avoiding withdrawing any of the interface between phases. This aqueous phase, which contained the RNA from the sample, was made into a concentration of 55% ethanol by addition of 1.22 volumes of ethanol.

Immediately after mixing, the sample was applied directly to a glass fiber column, as used in an RNAqueous Kit® (Ambion). The sample was passed through the filter by centrifugation at ~12,000×G for 1 min, then the filter was washed by the successive passage of three wash solutions through it. The collection tube was emptied between each wash, and each wash was passed completely through the filter at ~12,000×G for 1 min or longer, if required to pass all fluid. The first wash was with 0.5 ml of 1.6 M guanidinium isocyanate (GuSCN)/70% ethanol, the last two with 80% alcohol/0.1 M NaCl/4.5 mM EDTA/10 mM TrisHCl, pH 7.5. After the last wash was passed through the filter, the filter was re-centrifuged over an empty collection tube to remove all traces of ethanol.

Figure 2:
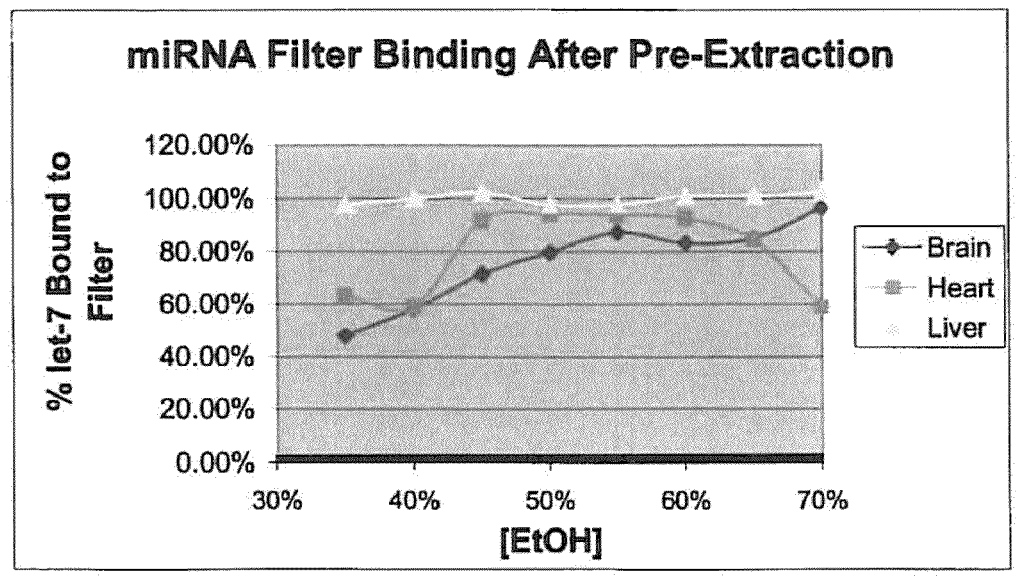
FIG. 2. Binding behavior of let-7 miRNA in phenol-chloroform extracts from mouse brain, heart, and liver at various ethanol concentrations. Absolute ethanol was added to lysates after extraction by phenol-chloroform (as in the standard procedure) to create the final ethanol concentrations indicated.
Figure 3:
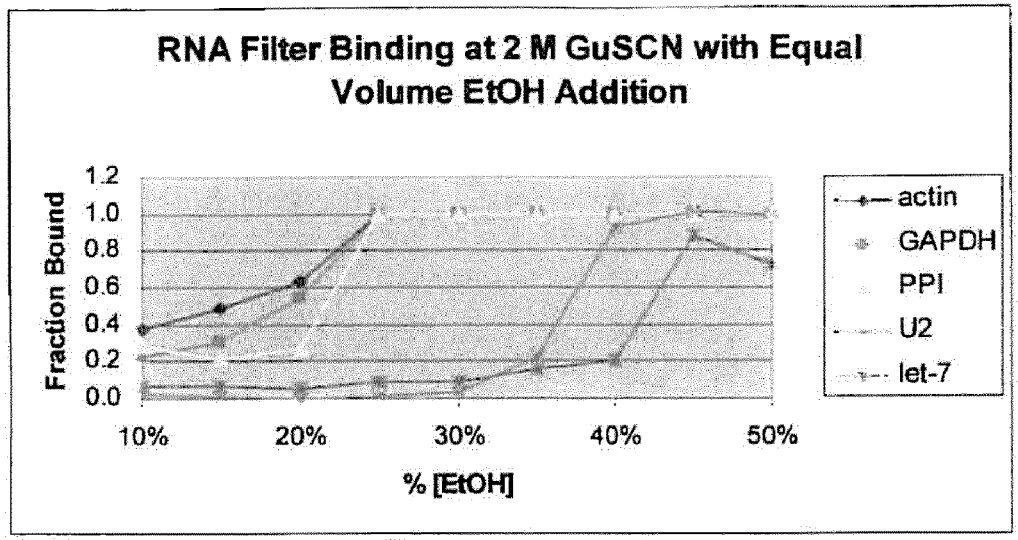
FIG. 3. Binding behavior of β-actin, GAPDH, PPI, U2, and let-7 at varying ethanol concentrations in the presence of 2M GuSCN, with ethanol concentration ajusted by addition of an equal volume of a 2× ethanol solution in water.
Figure 4:
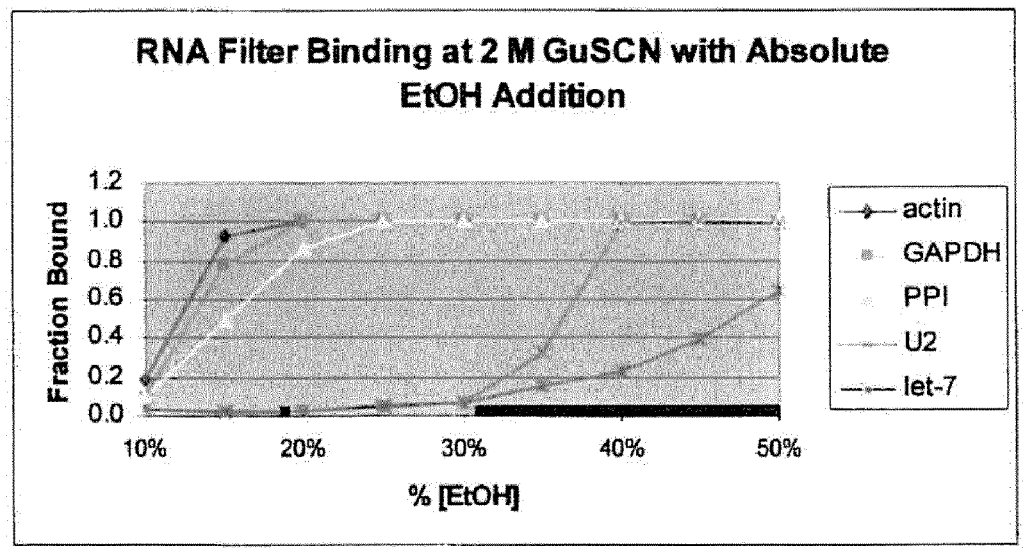
FIG. 4. Binding behavior of β-actin, GAPDH, PPI, U2, and let-7 at varying ethanol concentrations in the presence of 2M GuSCN, with ethanol concentration adjusted by addition of absolute ethanol.
Figure 5:
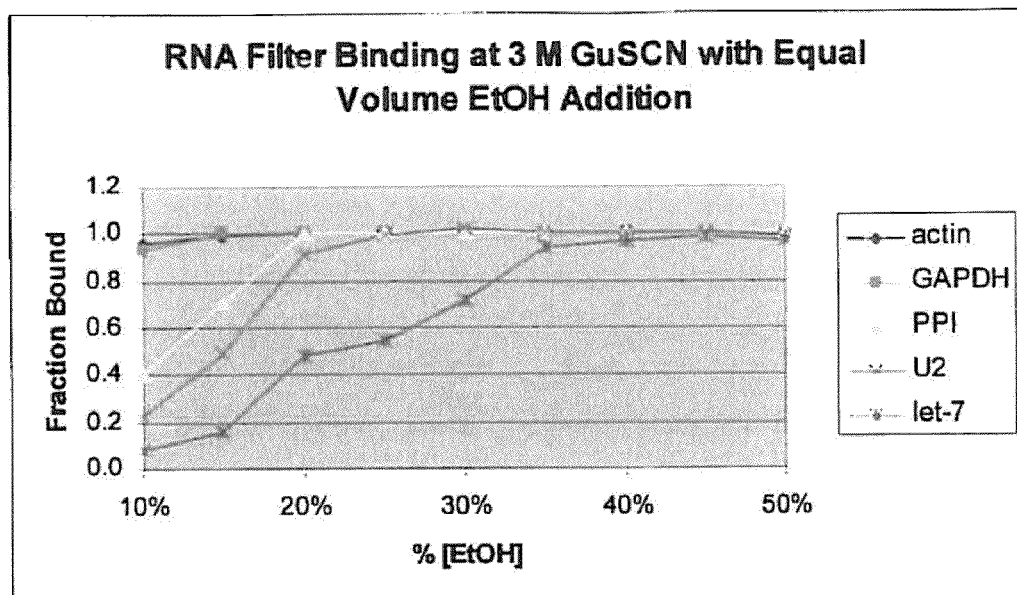
FIG. 5. Binding behavior of β-actin, GAPDH, PPI, U2, and let-7 at varying ethanol concentrations in the presence of 3M GuSCN, with ethanol concentration adjusted by addition of an equal volume of a 2× ethanol solution in water.
Figure 6:
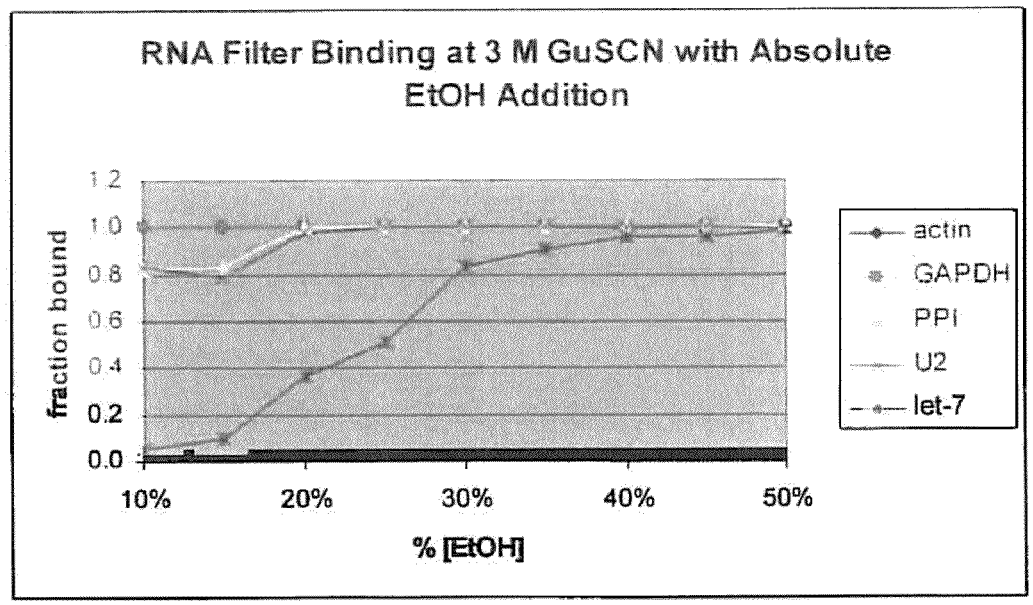
FIG. 6. Binding behavior of β-actin, GAPDH, PPI, U2, and let-7 at varying ethanol concentrations in the presence of 3M GuSCN, with ethanol concentration adjusted by addition of absolute ethanol.

The sample was then eluted off the filter with 100 μl of 0.1 mM EDTA, pH 8.0, which was applied directly to the filter at room temperature and centrifuged through into a fresh collection tube. FIG. 1 and FIG. 2 show the differences between preparations made from three different tissues, heart, brain, and liver, without and with the pre-extraction step. It can be seen that, in either circumstance, a substantial portion of the let-7 miRNA is captured at 55% ethanol.

Example 2

Detection of miRNAs Through Northern Blotting

For each RNA sample, 5 μl was combined with 5 μl of Gel Loading Dye II (Ambion). Prior to loading on a denaturing acrylamide gel, these samples were heated at 95° C. for 2-5 minutes. The standard gel was 15% acrylamide (monomer: bis ratio of 19:1), 7M urea, buffered with TBE (Tris-Borate-EDTA, Peacock and Dingman, 1967). The gel was routinely pre-run at 300-450 V for 30 minutes prior to loading the samples in sample buffer, which also contained bromphenol blue and xylene cyanol tracking dyes. The electrophoresis was performed at 300-450 V for 45-60 min, or until the bromphenol blue tracking dye was in the lower quadrant of the gel.

After electrophoresis, the gel apparatus was disassembled and the gel was electroblotted to a BrightStar-Plus Nylon membrane (Ambion). This procedure can be performed in a semi-dry apparatus using a stack of three sheets of Whatman filter paper (3 MM) soaked in 0.25×TBE above and below the gel sandwich at 200-400 mA for at least 0.2 A-hr. Extending this time does not lose sample. After blotting, the membrane was kept damp and UV crosslinked using a commercial crosslinking device (the Stratalinker™, Stratagene, Inc.)

The membrane was probed for the specific miRNA, let-7 (Pasquinelli et al., 2000) using an antisense probe that was 5' end-labeled by T4 Polynucleotide kinase.

In some cases other ubiquitous small RNAs were also probed for with antisense oligodeoxyribonucleotides at the same time. These included the U2 snRNA (Accession # X07913, complementary to the positions 28-42 of the 187 nt mouse U2 snRNA), U6 snRNA (Accession # V00853 or J00648, complementary to positions 83-103 of the 106 nt mouse RNA), and U43 snoRNA (Accession # AJ238853, complementary to positions 20-37 of the 62 nt human U43 RNA). All of these cross-hybridize readily between mouse and human. The procedure of Patterson and Guthrie (1987) was followed for prehybridization, hybridization, and washing (Patterson and Guthrie, 1987). The blots were prehybridized in {6×SSC, 10×Denhardt's solution, 0.2% SDS} at 65° C. for at least one hour, then 10 ml of hybridization solution added {6×SSC, 5×Denhardt's, 0.2% SDS} which contained 5' end-labeled let-7, U43, U6, and/or U2 antisense oligodeoxynucleotide probes (U43, U6, let-7 minimum=400,000 cpm; U2 minimum=200,000 cpm) and had been filtered (0.45 µm pore) prior to use. Hybridization was for 8-24 hr with agitation at room temperature. After hybridization, solutions were removed, and the blot washed 3 times for 5 minutes at RT with wash solution: {6×SSC, 0.2% SDS}, then once with the same wash solution at 42° C. After the final wash, the blots were wrapped in plastic wrap and exposed to a phosphorimager screen (Molecular Dynamics) as per the manufacturer's instructions to quantify the amount of signal present in each band. The amount of let-7 in the fraction eluted was often compared to that in the flow-through, providing a "% bound" figure, as given in FIG. 1, FIG. 2, FIG. 3, FIG. 4, FIG. 5, and FIG. 6. For other figures, the amount of let-7 was compared to other samples or given as absolute. See specific examples.

For some of the examples, a second Northern blot was made from an agarose gel system to look for the presence of larger RNA species. These were mRNAs for the ubiquitously-expressed genes cyclophilin (=Peptidylproline Isomerase or PPI), GAPDH and/or β-actin. The agarose gels were run and blotted using the NorthernMax Gly kit as described by Ambion. For probing the blot, antisense RNA probes were transcribed from templates supplied by Ambion (cat#'s 7675, 7431, 7423) and hybridized in Ultrahyb (Ambion), using all protocols as specified in Ambion literature.

Example 3

Enrichment of Small RNA Molecules

Frozen mouse brain, heart, liver, and kidney were processed separately according to the following protocol for enrichment of small RNAs.

Approximately one-half gram of frozen mouse (strain Swiss-Webster, 6-12 weeks old) tissue was crushed to fine powder under liquid nitrogen in a mortar. This powder was further dispersed in standard lysis buffer (4 M GuSCN; 0.1 M beta-mercaptoethanol; 0.5% N-lauroyl sarcosine; 25 mM Na-citrate, pH 7.2) by the use of a rotor-stator homogenizer with a 7 mm generator at high speed for ~30 sec.

After homogenization, 0.6 ml of the lysate was removed for this study. 60 µl of 2M Na-acetate, pH 4.0, was added to the lysate, followed immediately by 0.6 ml of acid phenol-chloroform. After 30 sec of vigorous agitation, the aqueous phase was separated by centrifugation at 16,000×G for 5 min. Four 100 µl aliquots of this aqueous phase were used in four separate separations. The four aliquots had 100 µl of 40%, 50%, 60%, and 70% ethanol added to each, then were passed through glass fiber filters as in the RNAqueous procedure (Ambion). The 20%, 25%, 30%, and 35% ethanol solutions that passed through these filters (the flow-through) was then adjusted to 55% ethanol final concentration by the addition of 156, 133, 111, and 88.9 µl of ethanol, respectively. All four samples were passed over separate glass fiber filter columns. The filters were then washed with 0.7 ml of 4 M guanidinium isocyanate (GuSCN)/70% ethanol, followed by two washes with 0.5 ml 80% alcohol/0.1 M NaCl/4.5 mM EDTA/10 mM TrisHCl, pH 7.5. After each wash was passed through the filter, the collection tube was emptied and replaced. Each wash was passed through the filter by centrifugation as per the RNAqueous protocol (Ambion). filter re-centrifuged over an empty collection tube to remove all traces of ethanol. The sample was then eluted off the filter with 100 µl of 0.1 mM EDTA, pH 8.0, which was applied directly to the filter at room temperature and centrifuged through into a fresh collection tube. The samples were examined by Northern blot, as described, and compared on the same gel to another sample that had been prepared from an equal volume of the same lysate using the Totally RNA™ kit from Ambion.

Figure 7:
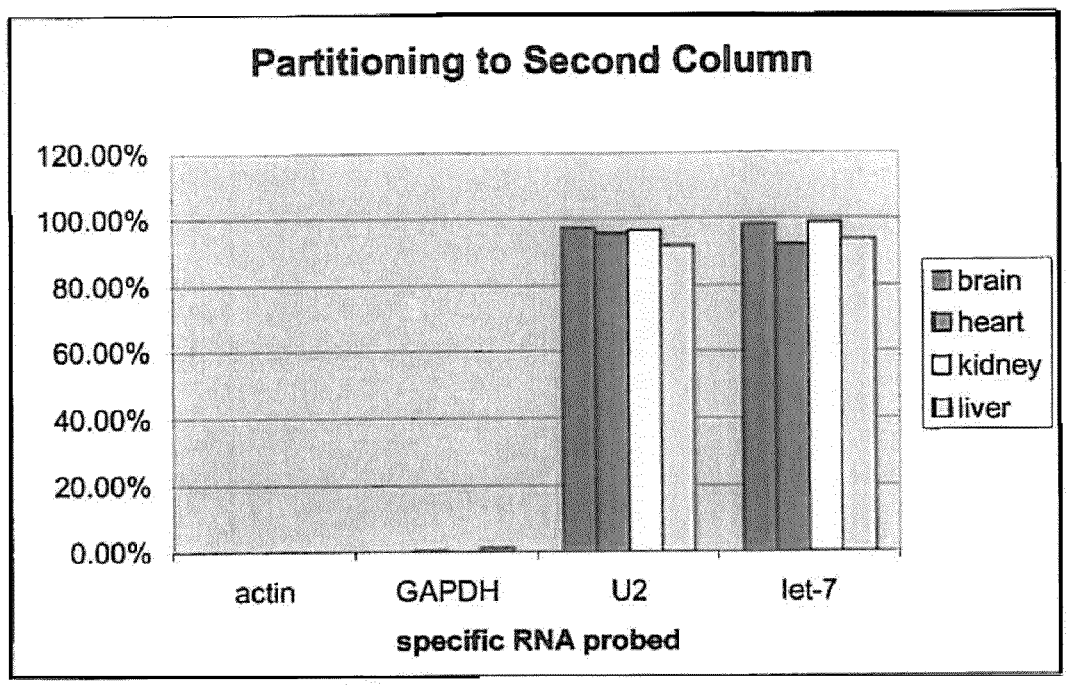
FIG. 7. Relative enrichment of β-actin, GAPDH, U2, and let-7 RNAs.

Using both agarose and acrylamide Northern blots, the levels of the β-actin, GAPDH, U2, and let-7 RNA species present in frozen mouse brain, heart, liver, and kidney were assayed in the material eluted from the first and second columns to determine the fraction recovered in the latter. These are shown on FIG. 7. The larger mRNA is completely removed from the small-RNA enriched fraction.

Figure 8:
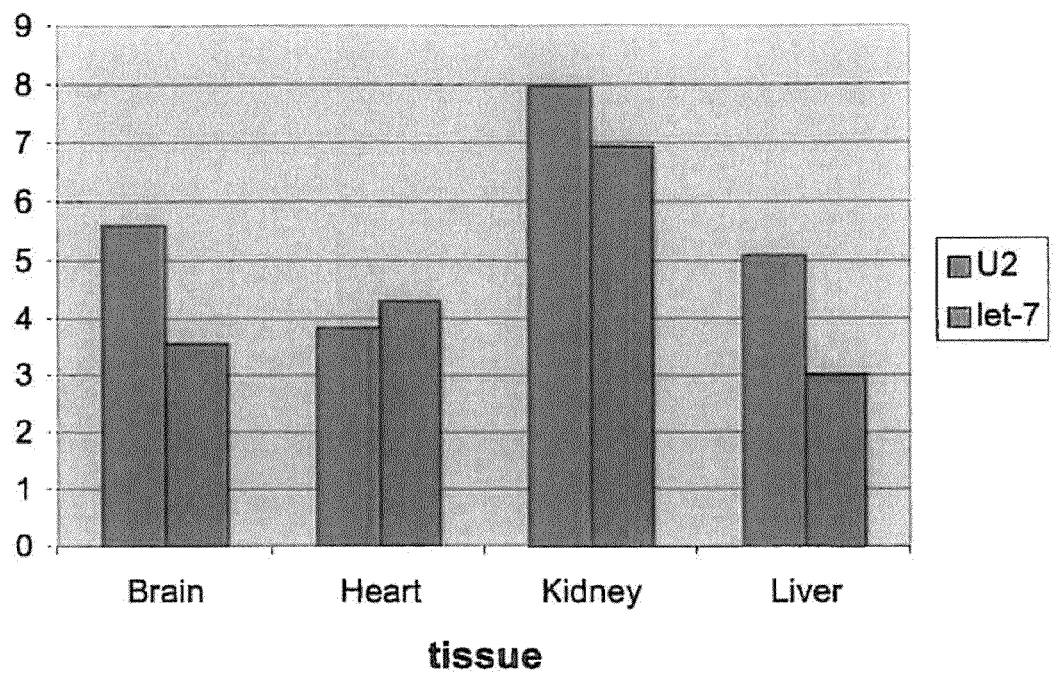
FIG. 8. Relative enrichment of U2 and let 7 RNAs.

FIG. 8 shows the relative enrichment of small RNAs using the method described in Example 3 as compared to the standard RNA isolation method. Here, samples of four common mouse tissues: brain, heart, kidney, and liver, were homogenized in standard lysis buffer as described in Example 1. After homogenization, two equal aliquots were taken of each lysate. One was subjected to a standard RNA preparative procedure using organic extraction and ethanol precipitation, using 4 volumes of ethanol to precipitate to ensure full recovery of small RNA species. The other aliquot was subjected to the enrichment procedure as described in Example 3. The concentration of RNA in each final sample was quantified using absorbence at 260 nm. One microgram of each sample was separated on a 15% denaturing polyacrylamide gel. This gel was electroblotted and the resultant Northern blot probed for let-7 and U2 as described in Example 2. The amount of each probe hybridized to the appropriate area of the blot was used to determine the relative amounts of each RNA in the 1 µg samples. The signal for the enriched samples was divided by the signal for the standard samples to provide the enrichment factors given in FIG. 8. Enrichment in this case was from ~3.5-8-fold by mass.

Example 4

Comparison to Standard Organic Extraction and Ethanol Precipitation

Figure 9:
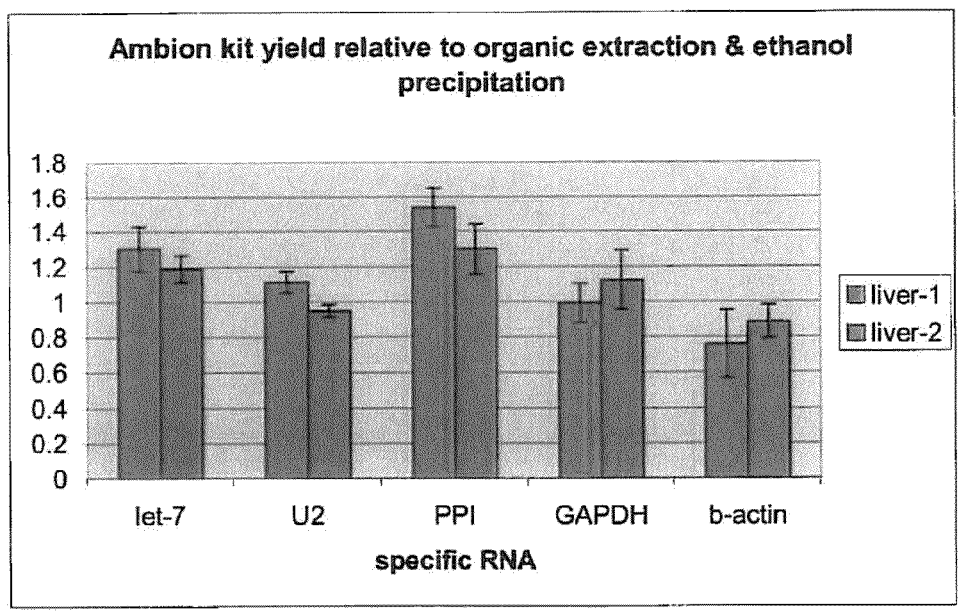
FIG. 9. Yield of current procedure compared to standard phenol-chloroform extraction and ethanol precipitation.

Samples from two mouse livers that had been stored frozen at ~80° C. were ground to a fine powder under liquid nitrogen and homogenized in 10 volumes (ml/g) the standard lysis buffer (4 M GuSCN; 0.1 M β-mercaptoethanol; 0.5% N-lauroyl sarcosine; 25 mM Na-citrate, pH 7.2) and then divided into four aliquots. One of the aliquots was extracted twice with two different phenol-chloroform solutions as described in the Totally RNA™ protocol (Ambion), and the other three were subjected individually to the standard AMIK procedure. The RNA pelleted from the Totally RNA™ procedure was redissolved in 100 µl of 0.1 mM EDTA, pH 8. The final elution for the AMIK samples was in the same volume and same solution. Samples were electrophoresed and blotted as described on both 15% acrylamide and 1% agarose gels. The appropriate blots were probed for β-actin, GAPDH, U2, U43, and let-7 as described. The recoveries of each RNA relative to the extraction procedure are summarized in the graph in FIG. 9. The yield from the invention generated amounts of small RNAs equal to or greater than the organic extraction procedure.

Example 5

Comparison to Standard Glass-Fiber Filter Purification

Frozen mouse liver and frozen mouse brain samples stored at ~80° C. were homogenized into standard lysis buffer at a ratio of 1 g tissue to 10 ml buffer. After homogenization, all lysates were stored on ice until one of two processing procedures was applied.

Figure 10:
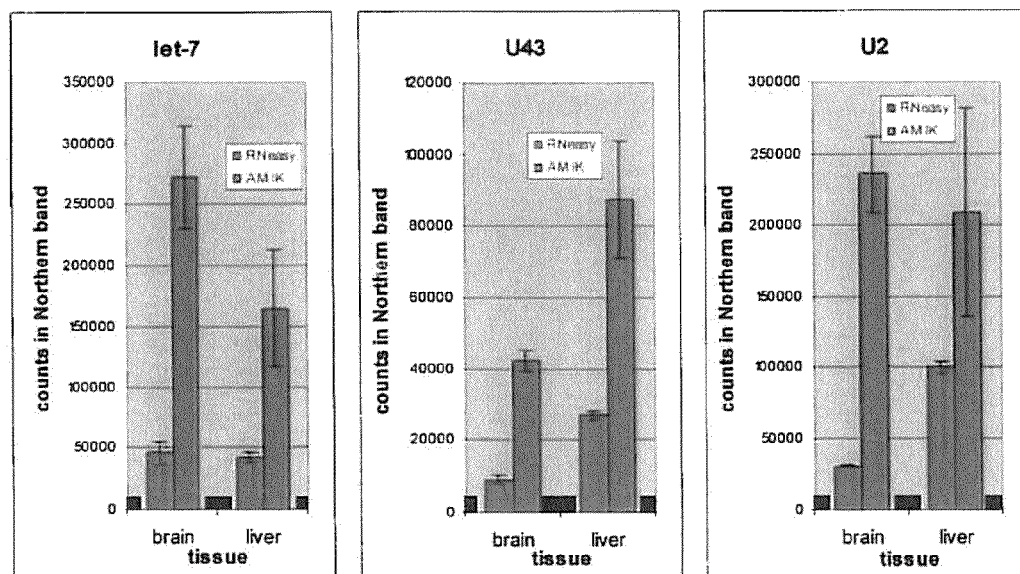
FIG. 10. Comparison of absolute yield of three small RNAs, let-7 (22 nt), U43 (62 nt), and U2 (187 nt), using the current process (Ambion microRNA Isolation Kit=AMIK) versus a glass fiber system currently available (RNeasy).

Starting with six aliquots of 100 µl from each parent lysate, 2 samples were processed by the RNeasy method from Qiagen, following their mini procedure precisely after addition of 250 µl of the Tissue Lysis Buffer (TLB) supplied with the kit. The final four aliquots from each tissue were prepared by the AMIK method previously described. The samples were all eluted in 100 µl of water. For analysis, 5 µl of each of the samples were analyzed by electrophoresis on 15% acrylamide gels and blotting, and the blots were probed for let-7, U43, and U2. After using phosphorimagery to quantify the bands, the signal levels were compared between the methods for each small RNA. These results are shown in FIG. 10. This invention was much more efficient at capturing all small RNAs than the standard glass-fiber filter extraction procedure. This inability to capture small molecules with a standard procedure is affected to some extent by the type of tissue as well, since the capture from liver lysate appears to be more efficient. This observation is consistent with our observations using raw lysate (FIG. 1).

Example 6

Efficiency of Small RNA Recovery from Raw Lysate in Three Different Tissues

Samples of frozen heart, liver, and brain from mice (strain Swiss-Webster, 6-12 weeks old) were each pulverized under liquid nitrogen to a powder. This powder was weighed frozen and 10 ml of lysis buffer per gram of tissue was added (weights ranged from 200 to 500 mg). Samples were homogenized with a rotor-stator homogenizer immediately after addition, then divided into 8×100 µl aliquots on ice. To these, 53.9, 66.7, 81.8, 100, 122.2, 150, 185.7, and 233.3 µl of absolute ethanol were added to make final concentrations of 35, 40, 45, 50, 55, 60, 65, and 70% ethanol. Each of these was passed over a glass fiber filter column as found in the RNAqueous® kit (Ambion), and the flow-through from this collected. The RNA in the flow-through was phenol-chloroform extracted and ethanol precipitated with four volumes of ethanol to ensure precipitation of small RNAs. After pelleting the RNA by 30 min of centrifugation at 16,000×G, the pellet was washed once with 80% ethanol and then redissolved in 60 µl of 0.5 mM EDTA, pH 8.0. The filters were washed three times, once with 0.7 ml of 4 M guanidinium isocyanate (GuSCN)/70% ethanol, followed by two washes with 0.5 ml 80% alcohol/0.1 M NaCl/4.5 mM EDTA/10 mM TrisHCl, pH 7.5. Each wash was performed as above, by centrifugation at 12,000×G for 1 min or sufficient time to clear all liquid through the filter, with collection tubes emptied after each. Samples were eluted using 2 separate additions of 30 µl of 0.1 mM EDTA, pH 8.0 which was applied directly to the filter after pre-warming to 95° C., each centrifuged through into the same fresh collection tube. Equal amounts (5 µl) of both the filter-bound-and-eluted and the flow-through were analyzed by Northern blot as described above. Since bound and flow-through were on the same blot, the amount of let-7 RNA bound could be calculated for each ethanol concentration with each tissue. This data is plotted in FIG. 1 and FIG. 2. It is apparent that the binding behavior for each tissue was different, in terms of the concentration of ethanol required to immobilize all let-7 RNA on the glass fiber filter. However, the maximum appears to be achieved for all tissues by 55% ethanol.

Example 7

Purification from Cultured Cells

Figure 11:
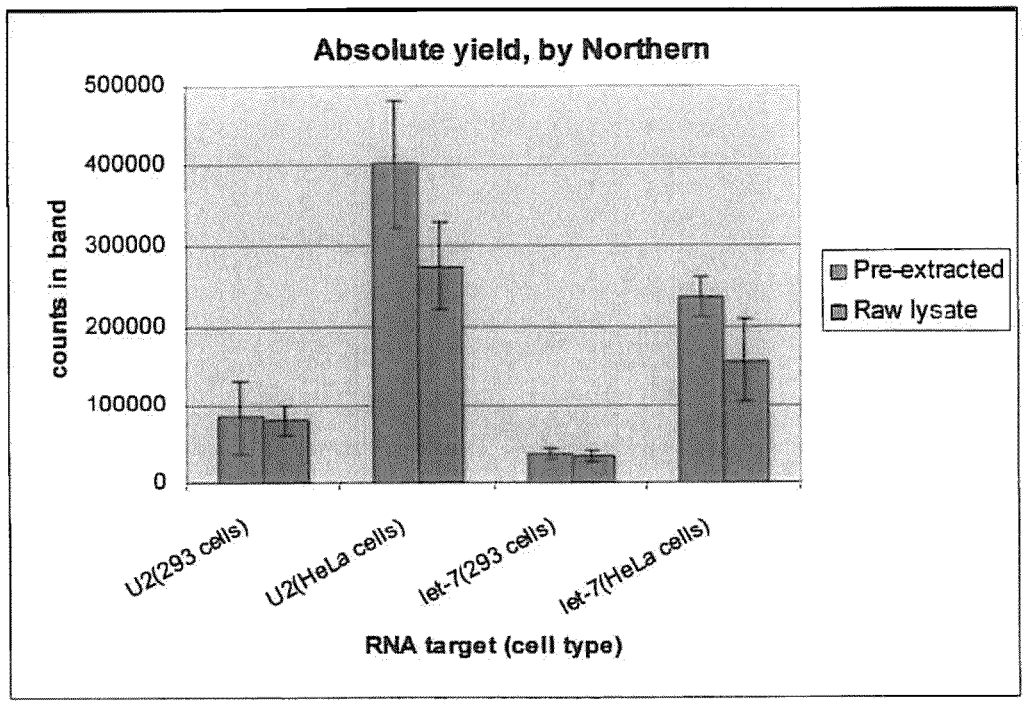
FIG. 11. Comparison of yield from cultured cells, with and without pre-extraction. The yield of both U2 and let-7 were determined.

Cells were collected from two lines, HEK-293 (derived from human embryonic kidney) or HeLa (human cervix) cells, from culture flasks by trypsinization. After counting, these cells were added at a level of about one million each to two 2 ml microcentrifuge tubes and pelleted by centrifugation. Supernatant was removed and the pelleted contents of each tube was resuspended in 700 µl of lysis buffer as described in the standard procedure (Example 1). The cells were lysed by agitating the tube vigorously for 30 sec rather than use of a homogenization apparatus. For each set, one set was immediately made about 55% ethanol by addition of 860 µl absolute ethanol. The other aliquot was processed as stated in the standard procedure: acidified by the addition of 70 µl 2 M Na-Acetate buffered to pH 4, followed by extraction with 700 µl acid phenol-chloroform, then addition of 860 µl ethanol to the recovered upper phase. Both samples were passed through glass-fiber filters, washed three times, and eluted with 100 µl 0.1 mM EDTA, pH 8 as described above. Five µl of each eluate was electrophoresed on a 15% acrylamide gel and Northern blotted for U2 and let-7. The levels of each, as determined from phosphorimagery of the blot, are shown in FIG. 11. The recovery of small RNAs from all the methods appears good, but recovery from HeLa cells was enhanced by the pre-extraction procedure.

Example 8

Pre-Extraction Using Different Salt Conditions

Figure 12:
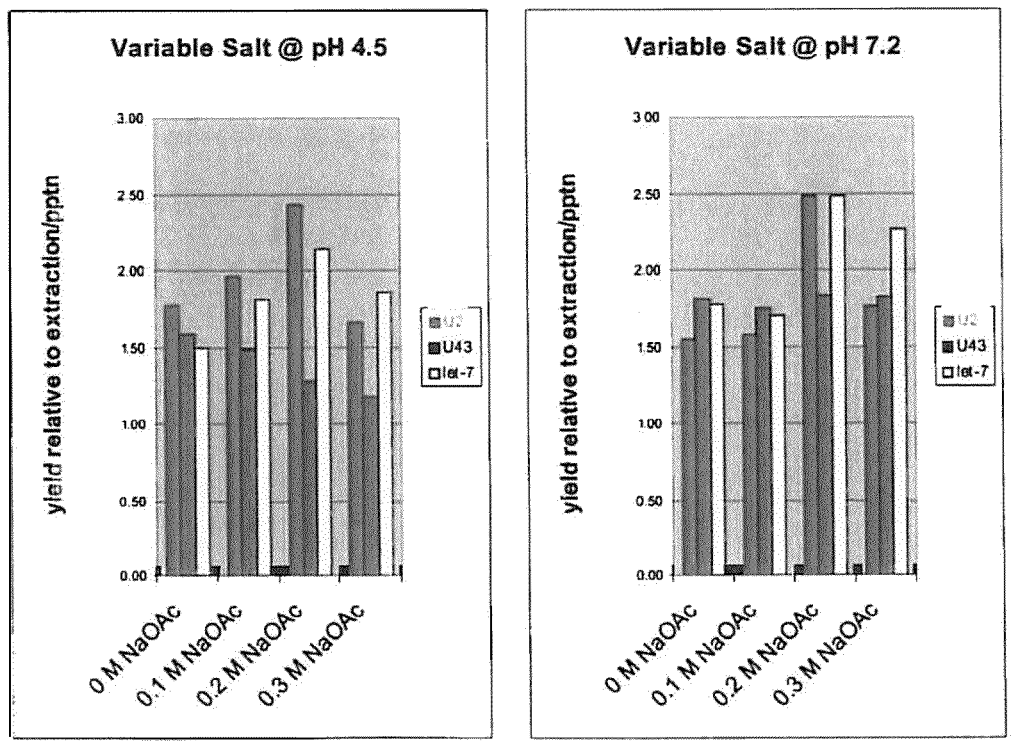
FIG. 12. Effects of different concentrations of $NaOOCH_3$ at two pHs for the phenol-chloroform extraction prior to glass immobilization on yield of U2, U43, and let-7.

Frozen mouse liver was homogenized into Lysis Buffer at 1.1× normal concentration minus Na-citrate (4.4 M GuSCN; 0.11 M β-mercaptoethanol; 0.55% N-lauroyl sarcosine). Immediately after homogenization, two 1.8 ml aliquots were removed from this lysate and 200 µl of 0.25M Na-citrate at either pH 7.2 or 4.5 was added to each. Four 400 µl aliquots were removed from these 2 ml portions, and 40 µl of either water, 1M, 2M, or 3M NaOOCCH$_3$ (sodium acetate, pH 4.5) was added to each of these, to give a final [NaOOCCH$_3$] of zero and about 0.1, 0.2, and 0.3 M. The samples were each extracted with 440 µl of acid phenol-chloroform and 300 µl of the upper phase recovered. This was made 55% in ethanol by the addition of absolute ethanol and purified over a glass-fiber filter column as described in the standard procedure. Each sample was applied to a 15% acrylamide gel, blotted and probed as described above. The levels of U2, U43, and let-7 determined for each are shown in the FIG. 12 graph. Yield appears to be roughly equivalent at both pH's (although U43 was variable), but the best yield appears in the presence of 0.2 M NaOOCCH$_3$ at both pH's.

Example 9

Binding of Small RNA Molecules at Different Guanidinium and Ethanol Concentrations Mouse liver was homogenized in standard lysis buffer and extracted with acid phenol-chloroform. The extracted lysate was divided in two portions. An equal volume was added to each consisting of either Lysis Buffer with no guanidinium (0.1 M β-mercaptoethanol; 0.5% N-lauroyl sarcosine; 25 mM Na-citrate, pH 7.2) or Lysis Buffer with 2 M GuSCN (2 M GuSCN; 0.1 M beta-mercaptoethanol; 0.5% N-lauroyl sarcosine; 25 mM Na-citrate, pH 7.2), creating solutions with a final [GuSCN] of 2 M and 3 M, respectively. These were then further divided into 18 aliquots of 200 μl each, and ethanol additions made in one of two manners. The first method was the addition of 22.2, 35.3, 50, 66.7, 85.7, 107.7, 133.3, and 200 μl of absolute ethanol. This gave final ethanol concentration of 10, 15, 20, 25, 30, 35, 40, 45, and 50%, with corresponding final guanidinium concentrations that decreased with increasing ethanol. (2.7, 2.55, 2.4, 2.25, 2.1, 1.95, 1.8, 1.65, and 1.5 M for 3 M initial concentration; 1.8, 1.7, 1.6, 1.5, 1.4, 1.3, 1.2, 1.1, and 1.0 M for 2 M initial concentration). The second method added equal volumes of ethanol solutions in water from 20-100% to give the same final ethanol concentrations, but with consistent guanidinium concentrations of 1.5 or 1 M within each series. After ethanol addition, each of these samples was bound to the glass-fiber filter and the standard procedure was followed. Samples were run on both acrylamide and agarose gels to assay for the presence of β-actin, GAPDH, PPI (cyclophilin), U2, and let-7. The binding behavior of each species as ethanol concentration increased was plotted for the four series in FIG. 3, FIG. 4, FIG. 5, and FIG. 6. From these series, it is demonstrated that differences exist in the behavior of the differently-sized RNA species, such that by manipulating both salt and ethanol concentration the binding of quite restricted size ranges of RNA molecules can be achieved, indicating more refined size-fractionation procedures can be performed.

Example 10

Use of Small RNAs to Probe Microarrays

Small RNAs enriched using procedures described in Examples 3 or 9 may be used in the microarray technologies described in the specification. In one example, the probes affixed to the microarray may contain sequences specifically designed to capture known miRNAs or siRNAs. Alternatively, the probes affixed to the microarray could be mRNA sequences to look for potential in vivo biological targets for miRNAs or siRNAs. The small RNA molecule population could be labeled radioactively or with tags that are reactive to light or able to bind secondary molecules capable of reacting with light. These direct or indirect labels could be attached through enzymatic means well-known to those of skill in the art such as: removal of the 5' phosphate with phospahtase followed by addition of modified phosphate with polynucleotide kinase; or addition to the 3' end of one or several tagged nucleotides with RNA ligase or polymerases such as poly-A polymerase.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references are specifically incorporated herein by reference.

U.S. Pat. No. 4,683,195
U.S. Pat. No. 4,683,202
U.S. Pat. No. 4,800,159
U.S. Pat. No. 4,883,750
U.S. Pat. No. 5,155,018
U.S. Pat. No. 5,234,809
U.S. Pat. No. 5,412,087
U.S. Pat. No. 5,445,934
U.S. Pat. No. 5,514,545
U.S. Pat. No. 5,545,522
U.S. Pat. No. 5,744,305
U.S. Pat. No. 5,843,650
U.S. Pat. No. 5,846,709
U.S. Pat. No. 5,846,783
U.S. Pat. No. 5,849,497
U.S. Pat. No. 5,849,546
U.S. Pat. No. 5,849,547
U.S. Pat. No. 5,858,652
U.S. Pat. No. 5,866,366
U.S. Pat. No. 5,912,148
U.S. Pat. No. 5,916,776
U.S. Pat. No. 5,916,779
U.S. Pat. No. 5,922,574
U.S. Pat. No. 5,928,905
U.S. Pat. No. 5,928,906
U.S. Pat. No. 5,932,451
U.S. Pat. No. 5,935,825
U.S. Pat. No. 5,939,291
U.S. Pat. No. 5,942,391
U.S. Pat. No. 5,945,525
U.S. Pat. No. 5,990,302
U.S. Pat. No. 6,043,354
U.S. Pat. No. 6,110,363
U.S. Pat. No. 6,180,778
U.S. Pat. No. 6,309,823
U.S. Pat. No. 6,316,193
U.S. Pat. No. 6,322,971
U.S. Pat. No. 6,324,479
U.S. Pat. No. 6,329,140
U.S. Pat. No. 6,329,209
U.S. Patent Appln. 2003/0104468
Boom et al., *J. Clin. Microbiol.,* 28(3):495-503, 1990.
Carrington et al., *Science* 301:336-338, 2003.
Chomczynski and Sacchi, *Anal. Biochem.,* 162(1):156-159, 1987.
DeRisi et al., *Nature Genetics,* 14:457-460, 1996.
Duggan et al., *Nat. Genet.,* 21(1):10-14, 1999.
Efstratiadis et al., *Proc. Natl. Acad. Sci. USA,* 73(7):2289-2293, 1976.
Europ. Appln. 329 822
Europ. Appln. No. 320 308
Fire et al., *Nature,* 391(6669):806-811, 1998.

Fodor et al., *Biochemistry*, 30(33):8102-8108, 1991.
Frohman, In: *PCR Protocols: A Guide To Methods And Applications*, Academic Press, N.Y., 1994.
GB Application No. 2 202 328
Gubler and Hoffmann, *Gene*, 25:263-269, 1983.
Hacia et al., *Nature Genet.*, 14:441-449, 1996.
Hamilton and Baulcombe, *Science*, 286(5441):950-952, 1999.
Higuchi et al., *Proc. Natl. Acad. Sci. USA*, 73(9):3146-3150, 1976.
Innis et al., *Proc. Natl. Acad. Sci. USA*, 85(24):9436-9440, 1988.
Ko et al., *Plant Mol. Biol.*, 14(2):217-227, 1990.
Kwoh et al., *Proc. Natl. Acad. Sci. USA*, 86:1173, 1989.
Lagos-Quintana et al., *Science*, 294(5543):853-858, 2001.
Land et al., *Nucleic Acids Res.*, 9(10):2251-2266, 1981.
Lau et al., *Science*, 294(5543):858-862, 2001.
Lee and Ambros, *Science*, 294(5543):862-864, 2001.
Lee et al., *Cell*, 75(5):843-854, 1993.
Maniatis et al., *Cell*, 8:163, 1976.
Maniatis, et al., In: *Molecular cloning*, A Laboratory Manual, Cold Spring Harbor Press, Cold Spring Harbor, N.Y., 1990.
Maskos et al., *Nucleic Acids Res.*, 20(7):1679-1684, 1992.
Ohara et al., *Proc. Natl. Acad. Sci. USA*, 86:5673-5677, 1989.
Okayama and Berg, *Mol. Cell. Biol.*, 2(2):161-170, 1982.
Pasquinelli et al., *Nature*, 408(6808):86-89, 2000.
Pasquinelli et al., *Nature*, 408(6808):86-89, 2000.
Patanjali et al., *Proc. Natl. Acad. Sci. USA*, 88(5):1943-1947, 1991.
Patterson and Guthrie, *Cell*, 49(5):613-624, 1987.
PCT Appln. PCT/US87/00880
PCT Appln. PCT/US89/01025
PCT Appln. WO 86/05815
PCT Appln. WO 88/10315
PCT Appln. WO 89/06700
PCT Appln. WO90/06045
Peacock and Dingman, *Biochemistry*, 6(6):1818-1827, 1967.
Pease et al., *Proc. Natl. Acad. Sci. USA*, 91:5022-5026, 1994.
Sambrook et al., In: *Molecular cloning*, Cold Spring Harbor Laboratory Press, Cold Spring Harbor, N.Y., 2001.
Schena, et al., *Science*, 270:467-470, 1995.
Shalon et al., *Genome Res.*, 6(7):639-645, 1996.
Shoemaker et al., *Nature Genetics*, 14:450-456, 1996.
Tang et al., *Genes Dev.*, 17(1):49-63, 2003.
Timmons, *Mol. Cell.*, 10(3):435-437, 2002.
Walker et al., *Proc. Natl. Acad. Sci. USA*, 89:392-396 1992.
Zamore et al., *Cell*, 101(1):25-33, 2000.

What is claimed is:

1. A method for isolating small RNA molecules from a sample comprising:
   a) lysing cells in a lysing solution to produce a lysate;
   b) extracting small RNA molecules from the lysate with an extraction solution comprising phenol;
   c) adding to the lysate an alcohol solution to form a lysate/alcohol mixture;
   d) applying the lysate/alcohol mixture to a first solid support;
   e) collecting flow-through lysate/alcohol mixture;
   f) adding to the flow-through lysate/alcohol mixture an alcohol solution;
   g) applying the lysate/alcohol mixture to a second solid support; and
   h) eluting small RNA molecules from the solid support with an ionic solution.

2. The method of claim 1, wherein the lysate/alcohol mixture applied to the first solid support is between about 20% to about 35% alcohol.

3. The method of claim 1, wherein the lysate/alcohol mixture applied to the second solid support is between about 35% to about 70% alcohol.

4. The method of claim 1, further comprising using or characterizing the small RNA molecules.

5. A method for isolating small RNA molecules from a sample containing cells, the method comprising:
   a) lysing the cells in a lysing solution to produce a lysate wherein the lysing solution comprises a chaotropic agent;
   b) extracting RNA molecules from the lysate with an extraction solution comprising phenol to form an aqueous phase containing RNA molecules;
   c) adding to the aqueous phase an alcohol solution to form a mixture of about 20% to about 35% alcohol;
   d) applying the mixture of about 20% to about 35% alcohol to a first solid support wherein small RNA molecules flow through the solid support and large RNA molecules bind to the solid support;
   e) collecting flow-through containing the small RNA molecules;
   f) adding to the flow-through containing small RNA molecules an alcohol solution to an alcohol concentration of about 55% to about 70%;
   g) applying the about 55% to about 70% alcohol solution containing small RNA molecules to a second solid support wherein small RNA molecules bind to the second solid support; and
   h) eluting small RNA molecules from the second solid support wherein small RNA molecules have 200 nucleotides or fewer, and large RNA molecules have greater than 200 nucleotides.

* * * * *